(12) United States Patent
Chan et al.

(10) Patent No.: US 8,009,297 B2
(45) Date of Patent: Aug. 30, 2011

(54) OPTICAL IMAGE MEASURING APPARATUS

(75) Inventors: Kinpui Chan, Ridgewood, NJ (US);
Masahiro Akiba, Fort Lee, NJ (US);
Yasufumi Fukuma, Fort Lee, NJ (US);
Hisashi Tsukada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 485 days.

(21) Appl. No.: 12/086,280

(22) PCT Filed: Nov. 7, 2006

(86) PCT No.: PCT/JP2006/322201
§ 371 (c)(1),
(2), (4) Date: Jun. 9, 2008

(87) PCT Pub. No.: WO2007/066465
PCT Pub. Date: Jun. 14, 2007

(65) Prior Publication Data
US 2009/0153873 A1    Jun. 18, 2009

(30) Foreign Application Priority Data

Dec. 7, 2005 (JP) ................................. 2005-353098
Dec. 7, 2005 (JP) ................................. 2005-353099

(51) Int. Cl.
*G01B 9/02* (2006.01)
(52) U.S. Cl. ...................................................... 356/495
(58) Field of Classification Search .................. 356/491, 356/497, 495
See application file for complete search history.

(56) References Cited

U.S. PATENT DOCUMENTS

| | | | |
|---|---|---|---|
| 6,606,158 B2* | 8/2003 | Rosenfeldt et al. | 356/477 |
| 6,769,769 B2* | 8/2004 | Podoleanu et al. | 351/221 |
| 6,856,398 B2* | 2/2005 | Ruchet | 356/453 |
| 7,061,621 B2* | 6/2006 | Krause | 356/491 |
| 7,075,658 B2* | 7/2006 | Izatt et al. | 356/479 |

(Continued)

FOREIGN PATENT DOCUMENTS
JP    2001-330558    11/2001
(Continued)

OTHER PUBLICATIONS

N. Tannno, "Optical coherence tomography and its application to living-body imaging," Japanese Journal of Optics (1999), vol. 28, pp. 116-125, with partial English translation thereof.

(Continued)

*Primary Examiner* — Gregory J Toatley
*Assistant Examiner* — Scott M Richey
(74) *Attorney, Agent, or Firm* — Edwards Angell Palmer & Dodge LLP

(57) ABSTRACT

Provided is an optical image measuring apparatus capable of obtaining a high-accuracy image without being influenced by a movement of an object to be measured. Flash light is emitted from a xenon lamp (2) and converted into broad band light by an optical filter (2A). A polarization characteristic of the flash light is converted into linear polarization by a polarizing plate (3). Then, the flash light is divided into signal light (S) and reference light (R) by a half mirror (6). A polarization characteristic of the reference light (R) is converted into circular polarization by a wavelength plate (7). The signal light (S) and the reference light (R) are superimposed on each other by the half mirror (6) to produce interference light (L). A CCD (23) detects interference light having the same characteristic as that of the produced interference light (L). The produced interference light (L) is divided into an S-polarized light component (L1) and a P-polarized light component (L2) by a polarization beam splitter (11). The polarized light components are detected by CCDs (21 and 22). A signal processing section (20) of a computer (30) forms an image of the object to be measured (O) based on detection signals from the CCDs (21, 22, and 23).

28 Claims, 10 Drawing Sheets

U.S. PATENT DOCUMENTS

| | | | |
|---|---|---|---|
| 7,286,226 B2* | 10/2007 | Takeuchi et al. | 356/364 |
| 7,426,021 B2* | 9/2008 | Cyr | 356/73.1 |
| 7,492,466 B2* | 2/2009 | Chan et al. | 356/497 |
| 7,548,320 B2* | 6/2009 | Chan et al. | 356/497 |
| 7,589,843 B2* | 9/2009 | Aiyer et al. | 356/504 |
| 7,599,069 B2* | 10/2009 | Toussaint et al. | 356/491 |
| 7,667,848 B2* | 2/2010 | Lee et al. | 356/451 |
| 7,710,577 B2* | 5/2010 | Yatagai et al. | 356/492 |
| 2006/0170932 A1* | 8/2006 | Hayashi et al. | 356/495 |
| 2007/0109553 A1* | 5/2007 | Feldchtein et al. | 356/492 |
| 2008/0007734 A1* | 1/2008 | Park et al. | 356/495 |
| 2008/0252901 A1* | 10/2008 | Shimizu et al. | 356/497 |

FOREIGN PATENT DOCUMENTS

| | | |
|---|---|---|
| JP | 2002-301049 | 10/2002 |
| JP | 2003-130790 | 5/2003 |
| JP | 2005-241464 | 9/2005 |
| JP | 2005-245740 | 9/2005 |

OTHER PUBLICATIONS

Yoshizawa, Seda, ed. "Optical Heterodyne Technology," New Technology Communications (2003), pp. 1-11, with partial English translation thereof.

K.P. Chan et al., "Micrometer-resolution, optical imaging of objects through highly scattering media using a heterodyne detector array," Electronics Letters (1994), vol. 30, No. 21, pp. 1753-1754.

M. Akiba et al., "Full-field optical coherent tomography by two-dimensional heterodyne detection with a pair of CCD cameras," Optics Letters (2003), vol. 28, No. 10, pp. 816-818.

L. Vabre et al., "Thermal-light full-filed optical coherent tomography," Optics Letters (2002), vol. 27, No. 7, pp. 530-532.

International Search Report mailed Jan. 16, 2007, issued on PCT/JP2006/322201.

* cited by examiner

OPTICAL IMAGE MEASURING APPARATUS

BACKGROUND OF THE INVENTION

1. Field of the Invention

The present invention relates to an optical image measuring apparatus configured to project light to a measurement object made of a light scattering medium in particular, measure the surface morphology or inner morphology of the measurement object by using the reflected light or transmitted light of the projected light, and form an image of the measured morphology.

2. Description of the Related Art

In recent years, attention has been given to the optical image measuring technology of forming an image of the surface or inside of a measurement object by using a laser light source or the like. This optical image measuring technology is not hazardous to human bodies unlike a conventional X-ray CT. Therefore, development of applications of this technology in the medical field has been expected in particular.

An example of a typical method of the optical image measuring technology is the low-coherence interferometry (may also be referred to as the optical coherence tomography or the like). This method employs the low coherence of a broadband light source having a broad spectral width, such as a super luminescent diode (SLD), and enables detection of reflected light from a measurement object or transmitted light therethrough at superior distance resolution on the order of μm (refer to Naohiro Tanno, "Kogaku" (Japanese Journal of Optics), Volume 28, No. 3, 116 (1999), for example).

FIG. 9 shows a basic configuration of a conventional optical image measuring apparatus based on a Michelson interferometer, as an example of an apparatus employing the low-coherence interferometry. An optical image measuring apparatus 1000 comprises a broadband light source 1001, a mirror 1002, a beam splitter 1003, and a photodetector 1004. A measurement object 1005 is made of a scattering medium. A light beam from the broadband light source 1001 is split by the beam splitter 1003 into two, i.e., a reference light R traveling to the mirror 1002 and a signal light S traveling to the measurement object 1005. The reference light R is a light reflected by the beam splitter 1003. The signal light S is a light transmitted through the beam splitter 1003.

Here, as shown in FIG. 9, the z-axis direction is defined as a traveling direction of the signal light S, and the x-y plane is defined as a plane orthogonal to the traveling direction of the signal light S. The mirror 1002 is movable in a direction indicated by a double-headed arrow in FIG. 9 (z-scanning direction).

The reference light R is subjected to Doppler frequency shift by z-scan when reflected by the mirror 1002. On the other hand, the signal light S is reflected by the surface and inner layers of the measurement object 1005 when projected to the measurement object 1005. Because the measurement object 1005 is made of a scattering medium, the reflected light of the signal light S is thought to have a diffusing wave front having random phases including multiple scatter. The signal light reflected by the measurement object 1005 and the reference light reflected by the mirror 1002 and subjected to the frequency shift are superimposed by the beam splitter 1003, thereby generating interference light.

In image measurement using the low-coherence interferometry, only a component of the signal light S interferes with the reference light R, that a difference in optical path length between the signal light S and the reference light R is within the coherence length (coherent distance) on the order of μm of the light source, and that has a phase correlation with the reference light R. That is, only a coherent signal light component of the signal light S selectively interferes with the reference light R. Based on this principle, by moving the position of the mirror 1002 by z-scanning and changing the optical path length of the reference light R, a light reflection profile of the inner layer of the measurement object 1005 is measured. Further, scan with the signal light S projected to the measurement object 1005 is performed in the x-y plane direction. By detecting the interference light with the photodetector 1004 while performing the scan in the z direction and x-y plane direction, and analyzing an electric signal (heterodyne signal) outputted as the result of the detection, a 2-dimensional tomographic image of the measurement object 1005 is acquired (refer to Naohiro Tanno, "Kogaku" (Japanese Journal of Optics), Volume 28, No. 3, 116 (1999)).

When the intensities of the reference light R and the signal light S superimposed by the beam splitter 1003 are denoted by symbols $I_r$ and $I_s$, and the difference in frequency between the reference light R and the signal light S and the difference in phase therebetween are denoted by symbols $f_{if}$ and $\Delta\theta$, a heterodyne signal as shown by the following formula is outputted from the photodetector (for example, refer to Yoshizawa and Seta "Optical Heterodyne Technology (revised edition)", New Technology Communications (2003), p. 2).

Formula (1)

$$i(t) \propto I_r + I_s + 2\sqrt{I_r I_s} \cos(2\pi f_{if} t + \Delta\theta) \qquad (1)$$

The third term of the right side of the formula (1) indicates an AC electric signal, and the frequency $f_{if}$ thereof is equal to the frequency of beat between the reference light R and the signal light S. The frequency $f_{if}$ of an AC component of the heterodyne signal is called a beat frequency or the like. Here, the AC component is equivalent to an interference component of the heterodyne signal whose intensity periodically changes with time. The first and second terms of the right side of the formula (1) indicate DC components of the heterodyne signal, and correspond to the signal intensity of a background light component of the interference light.

However, in order to acquire a 2-dimensional tomographic image by the conventional low-coherence interferometry, it is necessary to scan the measurement object 1005 with a light beam and thereby successively detect reflected light waves from respective sites of the measurement object 1005 in a depth direction (z direction) and a tomographic face direction (x-y plane direction). Therefore, it takes a long time to measure the measurement object 1005, and it is hard to shorten a measurement time in consideration of the measurement principle.

In view of such problems, an optical image measuring apparatus for shortening a measurement time has been proposed. FIG. 10 shows a fundamental configuration of an example of such an apparatus. An optical image measuring apparatus 2000 shown in FIG. 10 comprises a xenon lamp (a light source) 2001, a mirror 2002, a beam splitter 2003, a 2-dimensional photo-sensor array 2004 serving as a photodetector, and lenses 2006 and 2007. A light beam emitted from the light source 2001 is converted into a parallel light flux by the lenses 2006 and 2007, and a beam diameter thereof is widened. Then, the parallel light flux is split into two, i.e., the reference light R and the signal light S by the beam splitter 2003. The reference light R is subjected to Doppler frequency shift by z-scan of the mirror 2002. On the other hand, the signal light S enters the measurement object 2005 over a broad range of the x-y plane because the beam diameter has been widened. Therefore, the signal light S becomes reflected light containing information on the surface and inside of the measurement object 2005 in the incident range. The reference light R and the signal light S are superimposed by the beam splitter 2003, and detected by elements such as pixels and photo sensors arranged in parallel on the 2-dimensional photo-sensor array 2004. Thus, it becomes possible to acquire a 2-dimensional tomographic image of the measurement object 2005 in real time without scanning with a light beam.

As such a non-scanning type optical image measuring apparatus, an apparatus described in K. P. Chan, M. Yamada, and H. Inaba, "Electronics Letters", Vol. 30, 1753 (1994) has been known. The apparatus described in this document is configured to input a plurality of heterodyne signals outputted from a 2-dimensional photo-sensor array into a plurality of signal processing systems arranged in parallel and detect the amplitude and phase of each of the heterodyne signals.

However, in order to increase the spatial resolution of an image for this configuration, it is necessary to increase the number of the elements of the array, and moreover, it is necessary to prepare a signal processing system provided with the corresponding number of channels to that of the elements. Therefore, it is supposedly hard to practically use the apparatus in fields that require a high resolution image, such as a medical field and an industrial field.

Thus, the inventors have proposed a non-scanning type optical image measuring apparatus described below in Japanese Unexamined Patent Application Publication JP-A 2001-330558 (claims, paragraphs 0068 to 0084 of specification, and FIG. 1). This optical image measuring apparatus comprises a light source, an interference optical system, and a signal processor. The light source emits a light beam. The interference optical system splits the light beam emitted from the light source into two, i.e., a signal light passing through a subject arrangement position in which a subject is arranged and a reference light propagating on an optical path different from an optical path passing through the subject arrangement position, and superimposes the signal light having passed through the subject arrangement position and the reference light having propagated on the different optical path, thereby generating interference light. The interference optical system includes: a frequency shifter that shifts the frequency of the signal light and the frequency of the reference light relatively to each other; light cutoff devices that, for reception of the interference light, split the interference light into two, and periodically cut off the interference lights split into two, thereby generating two trains of interference light pulses with a phase difference of 90 degrees therebetween; and photo sensors that separately receive the two trains of interference light pulses, each of the photo sensors having a plurality of light receiving elements spatially arranged and separately detecting light receiving signals. The signal processor combines the plurality of light receiving signals obtained by the photo sensors, and generates signals corresponding to respective points of interest on a propagating path of the signal light, of the surface or inner layer of the subject arranged in the subject arrangement position.

This optical image measuring apparatus with the configuration to split the interference light generated from the reference light and the signal light into two and receive with the two photo sensors (i.e., 2-dimensional photo-sensor arrays) is configured to have the light cutoff devices positioned before the respective photo-sensor arrays and sample the interference lights. A phase difference of $\pi/2$ is set to sampling periods of the two split interference lights, whereby the intensities of the signal light and reference light composing a background light component of the interference light and phase quadrature components (i.e., sine component and cosine component) of the interference light are detected. Moreover, the intensity of the background light component contained in outputs from the photo-sensor arrays is subtracted from the outputs from the photo-sensor arrays, whereby two phase quadrature components of the interference light are calculated, and the amplitude of the interference light is obtained using the result of the calculation.

An available image sensor such as a charge-coupled device (CCD) camera has been widely used as the 2-dimensional photo-sensor array. However, a problem has been recognized conventionally that a currently available CCD camera cannot follow the beat frequency of a heterodyne signal on the order of several kHz to several MHz because of the low frequency response characteristic thereof. The feature of the optical image measuring apparatus described by the inventors in JP-A 2001-330558 is measurement performed by using the low frequency response characteristic based on the sufficient recognition of the above problem.

In the conventional optical image measuring apparatus as described above, about ten interference light pulses are received by the CCD and accumulated to form a single image. Application of this apparatus to ophthalmic measurement will cause a problem that, in a case where an eye moves because of eyeball movement, heartbeat or the like during detection of the about ten interference light pulses, the interference light is subjected to Doppler shift at the time of reflection on a fundus oculi and the frequency thereof is modulated, whereby the accuracy of a formed image is lowered.

This problem will arise not only in the medical field such as the ophthalmic field but also in various kinds of fields using an object that may move during measurement as a measurement target (for example, the biological field).

Further, there is a problem that about ten interference light pulses are necessary to form a single image as described above and control of open/close timing of the light cutoff device therefor is difficult.

Furthermore, there is a problem that it is necessary to turn on/off the light source in synchronization with the beat frequency of the heterodyne signal and control of the synchronization is difficult.

Besides, the conventional configuration has a problem that about ten interference light pulses are necessary to form a single image and it takes time to measure.

SUMMARY OF THE INVENTION

The present invention has been made to solve the aforementioned problems, and an object of the present invention is to provide an optical image measuring apparatus capable of shortening a measurement time.

Further, another object of the present invention is to provide an optical image measuring apparatus capable of forming a highly accurate image without being influenced by a movement of a measurement object.

Furthermore, another object of the present invention is to provide an optical image measuring apparatus capable of forming an image of a measurement object without executing complicated control of a light cutoff device or a light source.

In order to achieve the aforementioned objects, in a first aspect of the present invention, an optical image measuring apparatus comprises: a light-emitting part configured to emit a broadband light; a splitter configured to split the emitted broadband light into a signal light heading to a measurement object and a reference light heading to a reference object; a converter configured to convert a polarization characteristic of the signal light or the reference light; a superimposing part configured to superimpose one of the signal light returned from the measurement object and the reference light returned from the reference object onto the other to generate interference light, the one of the signal light and the reference light having the converted polarization characteristic; an extracting part configured to extract two different polarization components of the generated interference light; a first detector configured to detect one of the two polarization components having been extracted and output a first detection signal, and a second detector configured to detect the other and output a second detection signal; and an image formation processor configured to form an image of the measurement object, based on the first and second detection signals outputted by the first and second detectors.

Further, in a second aspect of the present invention, an optical image measuring apparatus according to claim 1 further comprises a third detector configured to detect light originating from the broadband light emitted by the light-emitting part and output a third detection signal, and the image formation processor forms the image of the measurement object, based on the first, second and third detection signals.

Furthermore, in a third aspect of the present invention, in an optical image measuring apparatus according to claim 2, the image formation processor includes: a background-light calculator configured to calculate a background light component of the interference light, based on the third detection signal; and an interference-component-intensity calculator configured to calculate a signal intensity of an interference component of each of the two polarization components, based on the calculated background light component and the first and second detection signals. The image formation processor forms the image of the measurement object, based on the calculated signal intensity of the interference component of each of the two polarization components.

Still further, in a fourth aspect of the present invention, in an optical image measuring apparatus according to claim 2, the image formation processor includes: a background-light calculator configured to calculate a background light component of the interference light, based on the third detection signal; and a phase-distribution calculator configured to calculate a spatial phase distribution of the interference light, based on the calculated background light component and the first and second detection signals. The image formation processor forms an image showing the calculated spatial phase distribution.

Still further, in a fifth aspect of the present invention, in an optical image measuring apparatus according to claim 2: the first, second and third detectors output the first, second and third detection signals, respectively, at a specific frame rate; the light-emitting part intermittently emits a flash light as the broadband light at a timing synchronized with the specific frame rate; and, for each of the flash lights emitted intermittently, the image forming processor forms the image of the measurement object, based on the first, second and third detection signals originating from the flash light.

Still further, in a sixth aspect of the present invention, an optical image measuring apparatus according to claim 2 further comprises an optical-path-length changer configured to change a difference in optical path length between the signal light and the reference light. The light-emitting part emits another flash light when the optical path length is changed after a flash light as the broadband light is emitted. The image formation processor forms another image of the measurement object, based on the first, second and third detection signals originating from the another flash light.

Still further, in an seventh aspect of the present invention, in an optical image measuring apparatus according to claim 6: the optical-path-length changer continuously changes the optical path length of the reference light; the light-emitting part intermittently emits the flash light; and the image formation processor forms an image of the measurement object, based on the first, second and third detection signals originating from each of the flash lights intermittently emitted.

Still further, in an eighth aspect of the present invention, in an optical image measuring apparatus according to claim 6: the optical-path-length changer intermittently changes the difference in optical path length; a controller is further comprised, which is configured to synchronize a timing of intermittent emission of the flash light by the light-emitting part with a timing of intermittent change of the difference in optical path length by the optical-path-length changer; and the image formation processor forms an image of the measurement object, based on the first, second and third detection signals originating from each of the flash lights emitted at the synchronized emission timing.

Still further, in a ninth aspect of the present invention, an optical image measuring apparatus according to claim 2 further comprises an exposure-time changer configured to change an exposure time for the polarization component by each of the first and second detectors. The image formation processor forms the image of the measurement object, based on the first and second detection signals originating from the polarization components detected in the changed exposure time and based on the third detection signal.

Still further, in a tenth aspect of the present invention, in an optical image measuring apparatus according to claim 9: the first and second detectors output the first and second detection signals, respectively, at a specific frame rate; and the exposure-time changer changes the exposure time by each of the first and second detectors to a time shorter than the specific frame rate.

Still further, in a eleventh aspect of the present invention, in an optical image measuring apparatus according to claim 9: the first and second detectors output the first and second detection signals, respectively, at a specific frame rate; the light-emitting part emits the broadband light whose emission time is shorter than the specific frame rate; and the exposure-time changer changes the exposure time by each of the first and second detectors to a time shorter than the emission time of the broadband light.

Still further, in a twelfth aspect of the present invention, an optical image measuring apparatus according to claim 1 further comprises an optical-path-length changing member configured to be insertable into and retractable from an optical path of the signal light or the reference light, thereby changing a length of the optical path. The image formation processor forms the image of the measurement object, based on the first and second detection signals outputted from the first and second detectors when the optical-path-length changing member is retracted from the optical path, and a fourth detection signal outputted by the first or second detector when the optical-path-length changing member is inserted into the optical path.

Still further, in a thirteenth aspect of the present invention, an optical image measuring apparatus according to claim 1 further comprises an optical-path-length changing member configured to be insertable into and retractable from an optical path of the signal light or the reference light, thereby changing a length of the optical path. The image formation processor forms the image of the measurement object, based on the first and second detection signals outputted from the first and second detectors when the optical-path-length changing member is inserted into the optical path, and a fourth detection signal outputted by the first or second detector when the optical-path-length changing member is retracted from the optical path.

Still further, in a fourteenth aspect of the present invention, in an optical image measuring apparatus according to claim 12, the image formation processor includes: a background-light calculator configured to calculate a background light component of the interference light, based on the fourth detection signal; and an interference-component-intensity calculator configured to calculate a signal intensity of an interference component of each of the two polarization components, based on the calculated background light component and the first and second detection signals. The image formation processor forms the image of the measurement object, based on the calculated signal intensity of the interference component of each of the two polarization components.

Still further, in a fifteenth aspect of the present invention, in an optical image measuring apparatus according to claim 13, the image formation processor includes: a background-light calculator configured to calculate a background light component of the interference light, based on the fourth detection signal; and an interference-component-intensity calculator configured to calculate a signal intensity of an interference component of each of the two polarization components, based on the calculated background light component and the first and second detection signals. The image formation processor forms the image of the measurement object, based on the calculated signal intensity of the interference component of each of the two polarization components.

Still further, in a sixteenth aspect of the present invention, in an optical image measuring apparatus according to claim 12, the image formation processor includes: a background-light calculator configured to calculate a background light component of the interference light, based on the fourth detection signal; and a phase-distribution calculator configured to calculate a spatial phase distribution of the interference light, based on the calculated background light component and the first and second detection signals. The image formation processor forms an image showing the calculated spatial phase distribution.

Still further, in a seventeenth aspect of the present invention, in an optical image measuring apparatus according to claim 13, the image formation processor includes: a background-light calculator configured to calculate a background light component of the interference light, based on the fourth detection signal; and a phase-distribution calculator configured to calculate a spatial phase distribution of the interference light, based on the calculated background light component and the first and second detection signals. The image formation processor forms an image showing the calculated spatial phase distribution.

Still further, in an eighteenth aspect of the present invention, in an optical image measuring apparatus according to claim 12: the first and second detectors output the first and second detection signals, respectively, at a specific frame rate; the light-emitting part intermittently emits a flash light as the broadband light at a timing synchronized with the specific frame rate, when the optical-path-length changing member is retracted from the optical path; and for each of the flash lights emitted intermittently, the image forming processor forms the image of the measurement object, based on the first and second detection signals originating from the flash light and based on the fourth detection signal.

Still further, in a nineteenth aspect of the present invention, in an optical image measuring apparatus according to claim 13: the first and second detectors output the first and second detection signals, respectively, at a specific frame rate; the light-emitting part intermittently emits a flash light as the broadband light at a timing synchronized with the specific frame rate, when the optical-path-length changing member is inserted into the optical path; and for each of the flash lights emitted intermittently, the image forming processor forms the image of the measurement object, based on the first and second detection signals originating from the flash light and based on the fourth detection signal.

Still further, in a twentieth aspect of the present invention, in an optical image measuring apparatus according to claim 12: the reference object is a reference mirror having a reflection face positioned orthogonally to the optical path of the reference light; a reference-mirror moving mechanism is further comprised, which is configured to move the reference mirror in a direction of the optical path of the reference light, thereby changing the optical path length of the reference light; the light-emitting part emits another flash light when the optical path length of the reference light is changed after a flash light as the broadband light is emitted, in a state where the optical-path-length changing member is retracted from the optical path; and the image formation processor forms another image of the measurement object, based on the first and second detection signals originating from the another flash light and based on the fourth detection signal.

Still further, in a twenty-first aspect of the present invention, in an optical image measuring apparatus according to claim 13: the reference object is a reference mirror having a reflection face positioned orthogonally to the optical path of the reference light; a reference-mirror moving mechanism is further comprises, which is configured to move the reference mirror in a direction of the optical path of the reference light, thereby changing the optical path length of the reference light; the light-emitting part emits another flash light when the optical path length of the reference light is changed after a flash light as the broadband light is emitted, in a state where the optical-path-length changing member is inserted into the optical path; and the image formation processor forms another image of the measurement object, based on the first and second detection signals originating from the another flash light and based on the fourth detection signal.

Still further, in a twenty-second aspect of the present invention, in an optical image measuring apparatus according to claim 20: the reference-mirror moving mechanism continuously moves the reference mirror in the optical path direction; the light-emitting part intermittently emits the flash light; and for each of the flash lights emitted intermittently, the image formation processor forms an image of the measurement object, based on the first and second detection signals originating from the flash light and based on the fourth detection signal.

Still further, in a twenty-third aspect of the present invention, in an optical image measuring apparatus according to claim 21: the reference-mirror moving mechanism continuously moves the reference mirror in the optical path direction; the light-emitting part intermittently emits the flash light; and for each of the flash lights emitted intermittently, the image formation processor forms an image of the measurement object, based on the first and second detection signals originating from the flash light and based on the fourth detection signal.

Still further, in a twenty-fourth aspect of the present invention, in an optical image measuring apparatus according to claim 20: the reference-mirror moving mechanism intermittently moves the reference mirror in the optical path direction; a controller is further comprised, which is configured to synchronize a timing of intermittent emission of the flash light by the light-emitting part with a timing of intermittent movement of the reference mirror by the reference-mirror moving mechanism; and the image formation processor forms an image of the measurement object, based on the first and second detection signals originating from each of the flash lights emitted at the synchronized emission timing and based on the fourth detection signal.

Still further, in a twenty-fifth aspect of the present invention, in an optical image measuring apparatus according to claim 21: the reference-mirror moving mechanism intermittently moves the reference mirror in the optical path direction; a controller is further comprised, which is configured to synchronize a timing of intermittent emission of the flash light by the light-emitting part with a timing of intermittent movement of the reference mirror by the reference-mirror moving mechanism; and the image formation processor forms an image of the measurement object, based on the first and second detection signals originating from each of the flash lights emitted at the synchronized emission timing and based on the fourth detection signal.

Still further, in a twenty-sixth aspect of the present invention, an optical image measuring apparatus according to claim 12 further comprises: an exposure-time changer configured to change an exposure time for the polarization component by each of the first and second detectors. The image formation processor forms the image of the measurement object, based on the first and second detection signals originating from the polarization components detected in the changed exposure time and based on the fourth detection signal.

Still further, in a twenty-seventh aspect of the present invention, an optical image measuring apparatus according to claim 13 further comprises: an exposure-time changer configured to change an exposure time for the polarization component by each of the first and second detectors. The image formation processor forms the image of the measurement object, based on the first and second detection signals originating from the polarization components detected in the changed exposure time and based on the fourth detection signal.

Still further, in a twenty-eighth aspect of the present invention, in an optical image measuring apparatus according to claim 26: the first and second detectors output the first and second detection signals, respectively, at a specific frame rate; and the exposure-time changer changes the exposure time by each of the first and second detectors to a time shorter than the specific frame rate.

Still further, in a twenty-ninth aspect of the present invention, in an optical image measuring apparatus according to claim 27: the first and second detectors output the first and second detection signals, respectively, at a specific frame rate; and the exposure-time changer changes the exposure time by each of the first and second detectors to a time shorter than the specific frame rate.

Still further, in a thirtieth aspect of the present invention, in an optical image measuring apparatus according to claim 26: the first and second detectors output the first and second detection signals, respectively, at a specific frame rate; the light-emitting part emits the broadband light whose emission time is shorter than the specific frame rate; and the exposure-time changer changes the exposure time by each of the first and second detectors to a time shorter than the emission time of the broadband light.

Still further, in a thirty-first aspect of the present invention, in an optical image measuring apparatus according to claim 27: the first and second detectors output the first and second detection signals, respectively, at a specific frame rate; the light-emitting part emits the broadband light whose emission time is shorter than the specific frame rate; and the exposure-time changer changes the exposure time by each of the first and second detectors to a time shorter than the emission time of the broadband light.

Still further, in a thirty-second aspect of the present invention, an optical image measuring apparatus according to claim 1 further comprises: a light-amount detector configured to detect a light amount of the broadband light emitted by the light-emitting part. The image formation processor regulates lightness of the formed image, based on the detected light amount.

The optical image measuring apparatus according to the present invention acts to split a broadband light emitted by the light-emitting part into a signal light heading to a measurement object and a reference light heading to a reference object, convert the polarization characteristic of the signal light or the reference light, and superimpose the signal light returned from the measurement object with the reference light returned from the reference object to generate interference light. Moreover, the optical image measuring apparatus acts to extract two different polarization components of the interference light, detect one of the two polarization components to output a first detection signal as well as detect the other to output a second detection signal, and form an image of the measurement object based on the first and second detection signals.

According to the optical image measuring apparatus acting in this manner, it is possible to simultaneously acquire two polarization components of interference light, and hence, it is possible to shorten a measurement time.

Further, according to the optical image measuring apparatus of the present invention, it is possible to simultaneously detect two polarization components of interference light, and there is no error in detection time between the two polarization components. Therefore, it is possible to form a highly accurate image without an influence of movement of the measurement object. In a case where two polarization components are not acquired simultaneously, the position of the measurement object at the time of detection of a first polarization component and the position of the measurement object at the time of detection of a second polarization component may be different, so that "flow" may be caused in an image of the measurement object. However, according to the optical image measuring apparatus of the present invention, it is possible to reduce the risk of occurrence of such "flow."

Furthermore, the optical image measuring apparatus of the present invention forms an image not by using a light-cutoff device (a shutter) for generating a plurality of interference-light pulses but by using the polarization characteristic of interference light, so that there is no need to execute complicated synchronization control between the light-cutoff device and the light source.

DETAILED DESCRIPTION OF THE PREFERRED EMBODIMENTS

Figure 1:
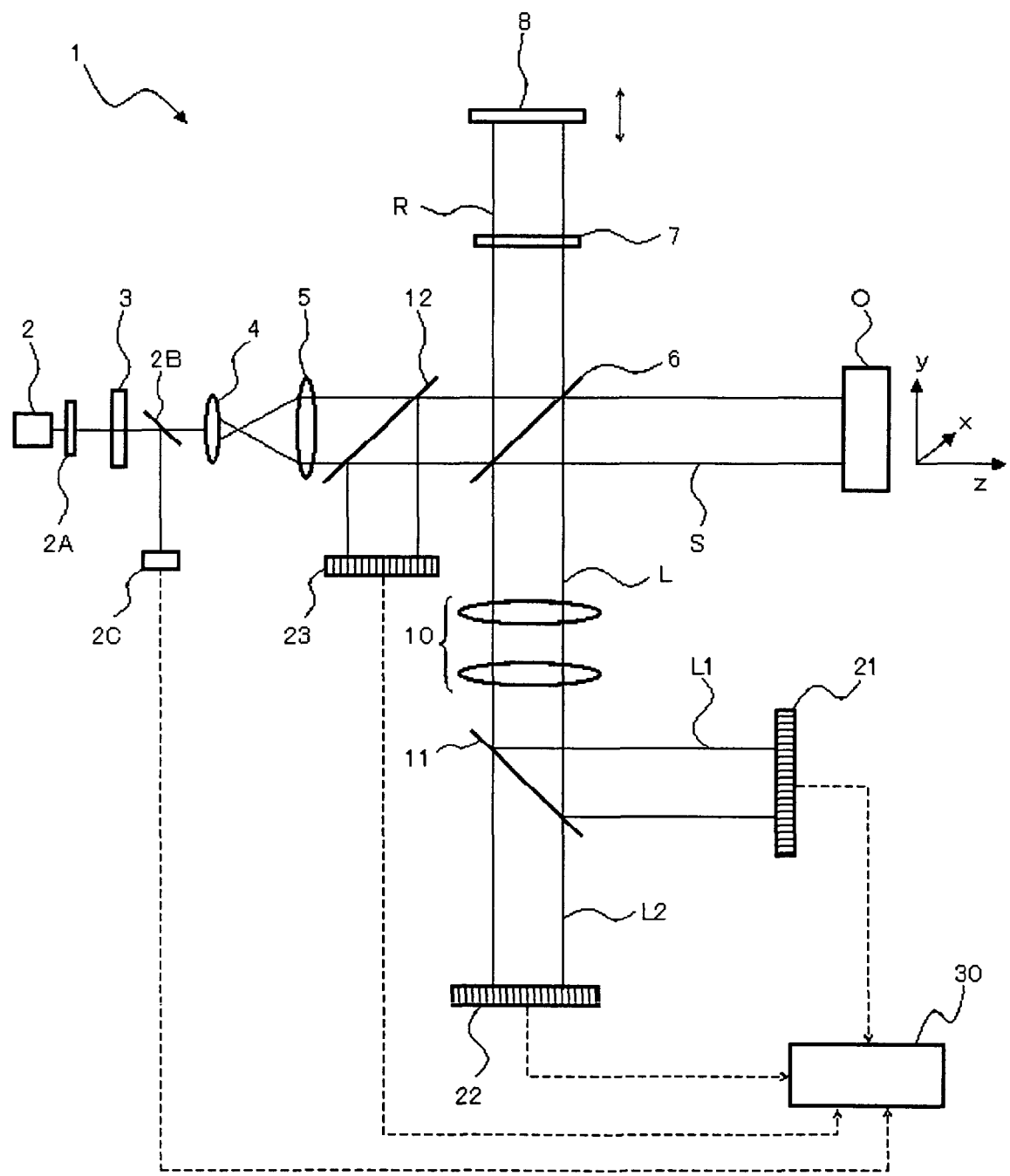
FIG. 1 is a schematic diagram showing an example of a configuration in an embodiment of an optical image measuring apparatus according to the present invention.

Hereinafter, an embodiment of an optical image measuring apparatus according to the present invention will be described in detail referring to the drawings.

First Embodiment

[Configuration of Apparatus]

FIG. 1 shows an example of a schematic configuration in an embodiment of the optical image measuring apparatus according to the present invention. An optical image measuring apparatus 1 shown in FIG. 1 is an apparatus that can be used for measurement of tomographic images or surface images of various kinds of measurement objects O in the field such as the medical field and the industrial field. This measurement object O is an object made of a scattering medium, such as a human eye in the medical field.

The optical image measuring apparatus 1 comprises a xenon lamp 2 configured to emit a flash light, and an optical filter 2A configured to convert the emitted flash light into a low-coherent broadband light. The xenon lamp 2 and the optical filter 2A correspond to an example of the "light-emitting part" configured to emit a broadband light in the present invention.

A polarizing plate 3 configured to convert the polarization characteristic of the flash light to linear polarization, a beam splitter 2B, lenses 4 and 5 configured to increase the diameter of the flash light and convert the flash light into a parallel light, a beam splitter 12, and a half mirror 6 are provided on the optical path of the flash light converted into the broadband light.

The flash light is split into a signal light S heading to the measurement object O and a reference light R heading to a reference mirror 8 by the half mirror 6. A wavelength plate 7 and the reference mirror 8 are provided on the optical path of the reference light R. The wavelength plate 7 acts to convert the polarization characteristic of the reference light R from linear polarization to circular polarization. Hereinafter, these members will be described in detail.

The xenon lamp 2 acts to emit a flash light as in a normal case, and corresponds to an example of the "light source" in the present invention. The xenon lamp 2 emits a sufficiently large amount of light as compared with an SLD used in a conventional optical image measuring apparatus. As the "light source" in the present invention, it is possible to use any light source that emits a sufficiently large amount of light as compared with an SLD used in general, such as a light-emitting diode (LED). Otherwise, it is possible to use an SLD when necessary.

The optical filter 2A is positioned on the optical path of the flash light emitted from the xenon lamp 2, and acts to convert the flash light into a low-coherent broadband light as described above.

In an xyz-coordinate system shown in FIG. 1, a traveling direction of the signal light S (i.e., flash light) is defined as a z-axis direction, and an oscillation plane of the signal light S that is orthogonal to the traveling direction is defined as an x-y plane. An x-axis direction and a y-axis direction are defined so as to align with an oscillation plane of an electric field component of the signal light S and an oscillation plane of a magnetic field component thereof, respectively.

The polarizing plate 3 is a polarization conversion element that transmits an oscillation component of a specific direction of the flash light emitted from the broadband light source 2. The polarizing plate 3 in this embodiment is configured to transmit an oscillation component of an angle direction forming 45° with the x-axis (and the y-axis) of the x-y plane. Consequently, the flash light transmitted through the polarizing plate 3 has linear polarization of 45°. That is, polarization components of the x-axis direction and the y-axis direction of this flash light have equal amplitudes. In other words, a P-polarization component and an S-polarization component of this flash light have equal amplitudes.

The half mirror 6 acts to split the flash light transmitted through the beam splitter 12 into the signal light S heading to the measurement object O and the reference light R heading to the reference mirror 8, and corresponds to an example of the "splitter" in present invention. The half mirror 6 transmits part (half) of the flash light to obtain the signal light S, and reflects the rest thereof to obtain the reference light R.

The half mirror 6 also acts as an example of the "superimposing part" in the present invention, configured to superimpose the signal light S back from the measurement object O and the reference light R back from the reference mirror 8 to generate an interference light L.

In this embodiment, about the half mirror 6 obliquely disposed on the optical path of the flash light emitted from the xenon lamp 2, the measurement object O is positioned on an extension of the optical path of the flash light, and the reference mirror 8 is positioned in a direction orthogonal to the optical path of the flash light, whereby a Michelson interferometer is formed. Therefore, in this embodiment, the "splitter" and the "superimposing part" are configured by (different reflection faces of) the single half mirror 6.

In a case where another type of interferometer such as a Mach-Zehnder interferometer is applied, the "splitter" and the "superimposing part" may be composed of different optical elements, respectively.

Further, as the "splitter" and the "superimposing part," it is possible to apply any non-polarization beam splitter having no influence on the polarization characteristics of the flash light, the signal light S and the reference light R.

The wavelength plate 7 corresponds to an example of the "converter" in the present invention, and is a polarization conversion element configured to convert the polarization characteristic of the reference light R having the linear polarization. In this embodiment, as the wavelength plate 7, a ⅛-wavelength plate that acts to make a phase difference of $\pi/4$ between a P-polarization component and an S-polarization component of light passing therethrough is used.

The reference light R passes through the wavelength plate 7 when traveling from the half mirror 6 to the reference mirror 8, and when reflected on the reference mirror 8 to travel back to the half mirror 6. Consequently, a phase difference of $\pi/2$ is applied to the reference light R having been reflected on the reference mirror 8 to travel back to the half mirror 6. Therefore, as in the case where a ¼-wavelength plate acts on the reference light R initially having linear polarization of 45°, the polarization characteristic of the reference light R having returned to the half mirror 6 is the circular polarization. In a case where another interferometer such as the Mach-Zehnder interferometer in which a reference light passes through a wavelength plate only once is used, a ¼-wavelength plate is used as the "converter."

The reference mirror 8 corresponds to an example of the "reference object" in the present invention, and has a reflection face orthogonal to the optical path direction (i.e., traveling direction) of the reference light R. The reference mirror 8 is moved in the optical path direction of the reference light R by a mechanism described later. Consequently, it becomes possible to extract a component reflected in a target depth region, from the reflected light of the signal light S in various depth (z-coordinate) regions of the measurement object O. The phase of the reference light R is shifted by the movement of the reference mirror 8.

The extraction of the component reflected in the target depth region will be described more specifically. Since the signal light S and the reference light R are each low-coherent light, only a portion of the signal light S propagating a distance substantially equal to that of the reference light R contributes to generation of the interference light L. In other words, only the reflected light in a depth region of the measurement object O, which is located at a distance substantially equal to the optical path length of the reference mirror 8, interferes with the reference light R to generate the interference light L. Therefore, by moving the reference mirror 8 to change the optical path length of the reference light R (i.e., performing z-scan), it is possible to sequentially extract light reflected in various depth regions of the measurement object O.

The optical image measuring apparatus 1 further comprises an imaging lens group 10 configured to image the interference light L generated by the half mirror 6 serving as the superimposing part, a polarization beam splitter 11 configured to split the optical path of the interference light L in accordance with the polarization characteristic, and CCD image sensors (merely referred to as CCDs) 21 and 22 provided on the respective optical paths of the split interference light L. The CCDs 21 and 22 each output a detection signal corresponding to detected light, to a computer 30.

Further, a CCD 23 is provided on an optical path branched by the beam splitter 12 obliquely provided between the lens 5 and the half mirror 6. Furthermore, a photodetector 2C such as a photodiode is provided on an optical path branched by the beam splitter 2B obliquely provided between the polarizing plate 3 and the lens 4. The CCD 23 and the photodetector 2C each output a detection signal corresponding to detected light, to the computer 30.

The polarization beam splitter 11 acts to extract a plurality of different polarization components from the interference light L, and corresponds to an example of the "extracting part" in the present invention. To be more specific, the polarization beam splitter 11 acts to reflect an S-polarization component L1 of the interference light L to cause the S-polarization component L1 to enter the CCD 21, and transmit a P-polarization component L2 and cause the P-polarization component L2 to enter the CCD 22. The S-polarization component L1 and the P-polarization component L2 of the interference light L have amplitudes (maximum intensities) equal to each other.

The CCD 21 detects the S-polarization component L1 of the interference light L extracted by the polarization beam splitter 11, performs photoelectric conversion to generate a detection signal, and outputs the detection signal to the computer 30. Similarly, the CCD 22 detects the extracted P-polarization component L2 of the interference light L, performs photoelectric conversion to generate a detection signal, and outputs the detection signal to the computer 30. The CCDs 21 and 22 correspond to examples of the "first detector" and "second detector," respectively, in the present invention. The detection signals outputted by the CCDs 21 and 22 correspond to examples of the "first detection signal" and "second detection signal," respectively.

The interference light generated from the signal light S transmitted through the half mirror 6 and the reference light R reflected by the half mirror 6 is reflected by the beam splitter 12, and enters the CCD 23. This interference light corresponds to an example of the "light corresponding to the broadband light" in the present invention, and has the same characteristic (particularly light intensity) as the interference light L heading to the imaging lens group 10. The CCD 23 detects this interference light, converts it into an electric signal (detection signal), and outputs the signal to the computer 30. The CCD 23 corresponds to an example of the "third detector" in the present invention, and the outputted detection signal corresponds to an example of the "third detection signal."

The CCDs 21, 22 and 23 are each capable of detecting light at a specific frame rate such as 30 frames per second, and outputting a detection signal.

The photodetector 2C detects part (i.e., light reflected by the beam splitter 2B) of the flash light emitted from the xenon lamp 2 and converted into the broadband light, performs photoelectric conversion to generate a detection signal, and outputs the detection signal to the computer 30. The detection signal has a signal intensity corresponding to the amount (intensity) of detected flash light. The photodetector 2C corresponds to an example of the "light-amount detector" in the present invention.

[Configuration of Control System]

Figure 2:
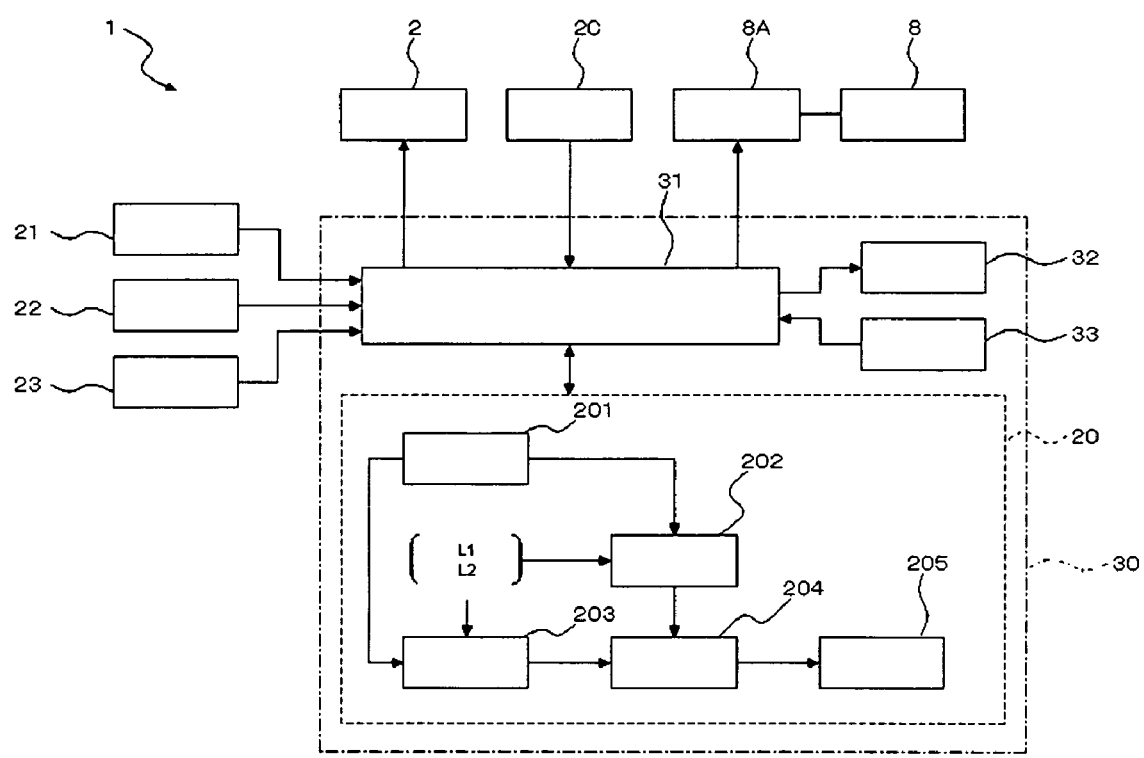
FIG. 2 is a schematic block diagram showing an example of a configuration of a control system in the embodiment of the optical image measuring apparatus according to the present invention.

FIG. 2 shows an example of a configuration of a control system of the optical image measuring apparatus 1. The optical image measuring apparatus 1 is provided with the computer 30.

As usual, the computer 30 includes a microprocessor such as a CPU, a RAM, a ROM, a hard disk drive, etc. Specific control programs, calculation programs and data such as various parameters are previously stored in the hard disk drive. The microprocessor loads these programs and data onto the RAM, and executes various control processes and calculation processes. The computer 30 includes a signal processor 20, a controller 31, a display 32, and an operation part 33.

The controller 31 controls each part of the optical image measuring apparatus 1, and includes a microprocessor, a RAM, a ROM, a hard disk drive, a power source circuit, etc. The controller 31 executes, for example, control of power supply to the xenon lamp 2, control of operation of a reference-mirror moving mechanism 8A, control for making the display 32 display various screens and images, and control of operation of the apparatus in accordance with operation signals from the operation part 33. The controller 31 corresponds to an example of the "controller" in the present invention.

The reference-mirror moving mechanism 8A is a mechanism configured to move the reference mirror 8 in an optical path direction of the reference light R in order to perform z-scan of the measurement object O. The reference-mirror moving mechanism 8A may continuously move the reference mirror 8, or intermittently move the reference mirror 8. In the case of continuously moving the reference mirror 8, the reference-mirror moving mechanism 8A includes a driving device such as a general motor and an ultrasonic motor, and a mechanism having various gears and shafts for transferring a driving force to the reference mirror 8. In the case of intermittently moving the reference mirror 8, the reference-mirror moving mechanism 8A includes a driving device such as a stepping motor and an ultrasonic motor, and a mechanism for transferring a driving force to the reference mirror 8. The reference-mirror moving mechanism 8A corresponds to an example of the "optical-path-length changer" in the present invention.

The detection signals outputted from the CCDs 21, 22 and 23 and the detection signal outputted from the photodetector 2C are inputted to the controller 31.

The display 32 is composed of any display device such as a liquid crystal display (LCD) and a CRT display. The operation part 33 is composed of any operation device or input device, such as a mouse, a keyboard, a trackball, a joystick and a control panel. In a case where a touch panel type display, a pen tablet or the like is used, the display 32 and the operation part 33 are integrally formed.

The signal processor 20 corresponds to an example of the "image formation processor" in the present invention, executes a process for forming an image based on the detection signals from the CCDs 21, 22 and 23, and includes a microprocessor, a RAM, a ROM, a hard disk drive, etc. The signal processor 20 is provided with a background-light calculator 201, an interference component intensity calculator 202, a phase-distribution calculator 203, an image forming part 204, and an image regulation processor 205.

The background-light calculator 201 calculates a background light component (noninterference component, DC component) of the interference light L based on the detection signal outputted from the CCD 23. As described above, the interference light detected by the CCD 23 has the same characteristic (particularly light intensity) as the interference light L. For example, the background-light calculator 201 integrates the detection signal from the CCD 23 for one wavelength (or an integral multiple thereof) to cancel an interference component (AC component) of the detection signal and extract a DC component thereof. The DC component corresponds to the background light component of the interference light L. The obtained background light component is inputted to the interference component intensity calculator 202. The background-light calculator 201 acting as described above corresponds to an example of the "background-light calculator" in the present invention.

The interference component intensity calculator 202 calculates the signal intensities of the interference components (i.e., phase quadrature components) of the S-polarization component L1 and the P-polarization component L2, respectively, based on the background light component (i.e., DC component) of the interference light L inputted from the background-light calculator 201, the detection signal inputted from the CCD 21 based on the S-polarization component L1 of the interference light L, and the detection signal inputted from the CCD 22 based on the P-polarization component L2.

To be specific, firstly, the interference component intensity calculator 202 subtracts the background light component from the detection signal based on the S-polarization component L1 to obtain the interference component of the S-polarization component L1. Similarly, the interference component intensity calculator 202 subtracts the background light component from the detection signal of the P-polarization component L2 to obtain the interference component of the P-polarization component L2. Since the interference component of the S-polarization component L1 and the interference component of the P-polarization component L2 are phase quadrature components, one of the interference components is a cosine wave while the other is a sine wave, and the interference components have the same phase.

The interference component intensity calculator 202 calculates the square sum of the two interference components and calculates the square root of the value of the square sum, thereby obtaining the amplitudes (i.e., signal intensities) of the interference components of the S-polarization component L1 and the P-polarization component L2, and obtaining the amplitude (i.e., signal intensity) of the interference light L. The obtained signal intensities are inputted to the image forming part 204. The interference component intensity calculator 202 acting as described above corresponds to an example of the "interference component intensity calculator" in the present invention.

Since the intensities of the detection signals change with time (refer to the formula (1) mentioned before) in first and second embodiments, the interference components of the S-polarization component L1 and P-polarization component L2 are "AC components" with temporal change. The "interference component" means both a signal component with temporal change and a signal component with spatial change (refer to a third embodiment).

The phase-distribution calculator 203 calculates a spatial distribution of phases of the interference light, based on the background light component of the interference light L inputted from the background-light calculator 201, the detection signal inputted from the CCD 21 based on the S-polarization component L1 of the interference light L, and the detection signal inputted from the CCD 22 based on the P-polarization component L2.

To be more specific, firstly, the phase-distribution calculator 203 calculates the ratio of the interference component of the S-polarization component L1 and the interference component of the P-polarization component L2, which are the cosine wave and the sine wave having the same phase, to obtain a tangent function. Since the amplitudes of the S-polarization component L1 and the P-polarization component L2 are equal, the tangent function does not depend on the amplitude of the interference light L (i.e., cancelled between numerator and denominator), and includes only phase information. The phase-distribution calculator 203 obtains the inverse function of the tangent function, thereby obtaining the phase information. The obtained phase information is outputted to the image forming part 204.

Considering the fact that a plurality of light receiving elements (pixels) are 2-dimensionally arranged on the light receiving faces of the CCDs 21 and 22, the phase information obtained by the phase-distribution calculator 203 presents a phase distribution state in a 2-dimensional coordinate plane defined on each of the light receiving faces of the CCDs 21 and 22. The phase-distribution calculator 203 acting as described above corresponds to an example of the "phase-distribution calculator" in the present invention.

The image forming part 204 performs a process for forming an image of the measurement object O, based on the signal intensities of the interference components of the S-polarization component L1 and the P-polarization component L2 of the interference light L inputted from the interference component intensity calculator 202. The image forming part 204 forms an image presenting the spatial phase distribution of the interference light L, based on the phase information inputted from the phase-distribution calculator 203.

The signal intensities of the interference components of the S-polarization component L1 and the P-polarization component L2 of the interference light L inputted from the interference component intensity calculator 202 are obtained for each pixel on the light receiving faces of the CCDs 21 and 22. The image forming part 204 designates a brightness value corresponding to the signal intensity of the interference component of the polarization component for each pixel, thereby forming a tomographic image expressing a shape of the measurement object O at a specific depth (i.e., z-coordinate value). The tomographic image is a monochrome contrast image. By designating a red (R) value, a green (G) value and a blue (B) value corresponding to the signal intensity of the interference component of the polarization light component, a color image can be formed.

Next, a process for forming the image presenting the spatial phase distribution will be described. Since the interference light L is generated based on the flash light from the xenon lamp 2, the phase information obtained by the phase-distribution calculator 203 is an instantaneous phase value. Therefore, the phase information is thought to be uniform regardless of pixel positions of the CCDs 21 and 22.

In consideration of this assumption, for example, with reference to phase values detected for pixels located at specific points on the light receiving faces of the CCDs 21 and 22, the image forming part 204 obtains a difference in phase between values of detection signals for the respective pixels. Then, the image forming part 204 designates brightness (i.e., reference brightness) for the reference phase value, and designates a brightness value for each pixel in accordance with the obtained phase difference. Consequently, an image representing a spatial distribution of the phase difference of the interference light L is formed.

The image regulation processor 205 acts to regulate the luminance of the image formed by the image forming part 204, based on the amount of the flash light detected by the photodetector 2C. Here, the term "luminance" means brightness in the case of a monochrome image, and brightness or lightness (i.e., maximum value of the brightness of each of R, G and B) in the case of a color image. An image subjected to luminance regulation is an image formed reflecting the signal intensity (i.e., amplitude) of the interference light L (Therefore, the image presenting the spatial phase distribution is exepted.

The amount of the flash light emitted from the xenon lamp 2 varies every time the light is emitted. The image regulation processor 205 regulates the luminance of the image based on the amount of flash light emitted at the time of image measurement to obtain an image whose luminance is maintained at a constant level. The action of the image regulation processor 205 is particularly effective in the case where plural images are to be obtained for the measurement object O.

Upon receiving the image formed by the image forming part 204, the image regulation processor 205 uses the light amount value detected by the photodetector 2C at the time of image measurement, and thereby corrects the brightness value or lightness value of each pixel composing the image.

A specific example of this method will be described. First, a reference light amount value Q0 of the flash light is set in advance. When the amount of light detected by the photodetector 2C is Q, the image regulation processor 205 corrects the brightness value (or the lightness value) $L(x, y)$ of each pixel of the image formed by the image forming part 204 to $(Q0/Q) \times L(x, y)$.

Consequently, even when the amount of light Q is larger than the reference light amount value Q0, and the image becomes brighter than the reference, or even when the amount of light Q is smaller than the reference light amount value Q0, and thus, the image becomes darker than the reference, it is possible to obtain an image whose luminance is substantially equal to that in the case of measurement using the reference light amount value. Such the method can be applied even in the case where an image is formed or even in the case where plural images are formed.

When plural images (for example, at different depths) are formed for the measurement object O, the following method can be also used as another specific example of the image luminance regulation processing. When N-sheets of images are to be obtained for the measurement object O, for example, a light amount value of flash light detected at the time of measurement of an ith image is set as a reference light amount value Qi (i=any one of 1 to N). In addition, a detection light amount value obtained at the time of measurement of a jth (j=1 to N, j≠i) image is expressed by Qj. In this case, the image regulation processor 205 regulates a brightness value (or lightness value) $Lj(x, y)$ of each pixel of the jth image to $(Qi/Qj) \times Lj(x, y)$. Therefore, the luminance of each of the N-images can be made substantially equal to the luminance of the ith image.

It is also possible to regulate a brightness values (or lightness values) of plural images at a specific pixel position be compared with one another and the luminance of each of the images be regulated using, for example, an average value of the brightness values as the reference light amount value.

[Operation Mode]

An operation mode of the optical image measuring apparatus 1 of this embodiment configured as described above will be described. Hereinafter, an operation example in the case of forming N sheets of images will be described.

First, the controller 31 controls the xenon lamp 2 to emit a flash light for forming a first image, and also controls the reference-mirror moving mechanism 8A to start continuous movement of the reference mirror 8 at a constant speed.

The flash light is converted into a low-coherent broadband light by the optical filter 2A, and the polarization characteristic thereof is converted to linear polarization by the polarizing plate 3. Part of the light is reflected by the beam splitter 2B, and the amount of the light is detected by the photodetector 2C. The detected light amount value is sent to the computer 30 and stored in (a RAM or a hard disk drive of) the controller 31.

The flash light having passed though the beam splitter 2B is increased in diameter by the lenses 4 and 5, and is converted into a parallel light. Then, the light passes through the beam splitter 12 and heads to the half mirror 6.

The half mirror 6 splits the flash light into the signal light S and the reference light R. The signal light S advances toward the measurement object O. Then, the signal light S is reflected at various depth positions of the measurement object O, and returns to the half mirror 6. While the reference light R are reciprocating between the half mirror 6 and the reference mirror 8, the polarization characteristic thereof is converted to circular polarization by the wavelength plate 7.

The half mirror 6 superimposes the signal light S having returned from the measurement object O with the circularly-polarized reference light R having returned from the reference mirror 8, thereby generating the interference light L. Because the signal light S and the reference light R are low-coherent, the interference light L includes information at a depth position of the measurement object O that is located at a substantially equal distance to a distance between the half mirror 6 and (the reflection face of) the reference mirror 8 at the time when the reference light R is reflected by the reference mirror 8. (In other words, the interference light L includes information at a depth position substantially corresponding to the width of a coherence length of the broadband light.)

At this moment, interference light having the same characteristic as the interference light L is generated to head to the beam splitter 12. Part of the generated interference light is reflected by the beam splitter 12 and detected by the CCD 23. The CCD 23 transmits a detection signal corresponding to the detected interference light, to the computer 30.

On the other hand, the interference light L is converted from the parallel light into focused light by the imaging lens group 10 and split into the S-polarization component L1 and the P-polarization component L2 by the polarization beam splitter 11. The S-polarization component L1 is detected by the CCD 21 and the P-polarization component L2 is detected by the CCD 22. The CCDs 21 and 22 transmit the detection signals to the computer 30, respectively.

The controller 31 sends the first detection signals from the CCDs 21, 22 and 23 and the detection signal from the photodetector 2C to the signal processor 20. When a specific time elapses after the emission of the flash light for the first image measurement, the controller 31 causes the xenon lamp 2 to emit a flash light for second image measurement. The second image measurement is performed as in the first image measurement. The emission timing of the flash light is synchronized with the frame rate (for example, 30 frames per second) of the CCDs 21, 22 and 23 by the controller 31.

Hereinafter, an operation of the signal processor 20 for forming the first image will be described. First, the background-light calculator 201 obtains the background light component of the interference light L based on the detection signal from the CCD 23. Next, the interference component intensity calculator 202 obtains the signal intensity of the interference component of the S-polarization component L1 and the signal intensity of the interference component of the P-polarization component L2, based on the background light component and the detection signals of the S-polarization component L1 from the CCD 21 and the P-polarization component L2 from the CCD 22. Next, the image forming part 204 forms an image G1 at a depth z=z1 of the measurement object O, based on the calculated signal intensities of the interference components of the S-polarization component L1 and the P-polarization component L2.

On the other hand, the phase-distribution calculator 203 calculates the spatial distribution of phases of the interference light L at the depth z=z1 of the measurement object O, based on the detection signals from the CCDs 21 and 22. The image forming part 204 forms an image P1 presenting the spatial distribution of the phases of the interference light L.

The above-mentioned process is executed for each depth z=z1 to zN, whereby N sheets of images G1 to GN and N sheets of images P1 to PN are formed. In the controller 31, light amount values Q1 to QN of the flash light at the time of measurement of the images G1 to GN are stored. The light amount values Q1 to QN are stored so as to be associated with the corresponding images G1 to GN.

A light amount value Qi of the flash light detected at the time of measurement of any image Gi of the N sheets of images G1 to GN is set as a reference light amount value. The image Gi as a reference image may be selected by a user, or may be automatically selected. In an example of the automatic selection, it is possible to compare brightness values (lightness values) of the images G1 to GN at a specific pixel with each other, and set an image having an intermediate brightness value as the reference image. The selection process is executed by, for example, the controller 31.

Assuming a light amount value detected at the time of measurement of a jth image Gj is denoted by Qj (j=1 to N, j≠i), the image regulation processor 205 corrects a brightness value (or a lightness value) Lj(x, y) of each pixel of the image Gj to (Qi/Qj)×Lj(x, y). Consequently, it is possible to make the luminance of each of the N sheets of images G1 to GN substantially equal to the luminance of the ith image Gi for reference.

The images G1 to GN thus formed are stored in, for example, the hard disk drive of the controller 31. In a case where a storage device such as an image database is connected to the computer 30, it is possible to store the images G1 to GN in the storage device. In a case where the computer 30 is connected to a network such as a LAN, the images may be stored in (a database of) a server on the network.

[Another Operation Mode]

In the above-mentioned operation mode, while the reference mirror 8 is continuously moved at a constant speed to perform z-scan, the flash light is emitted at a timing synchronized with the frame rate of the CCDs 21, 22 and 23, whereby the plurality of images G1 to GN of the measurement object O at different depths z=z1 to zN are formed.

On the other hand, in an operation mode described below will be described a configuration that while moving the reference mirror 8 intermittently to perform z-scan, emitting the flash light at a timing synchronized with the frame rate of the CCDs 21, 22 and 23, thereby forming the plurality of images G1 to GN of the measurement object O at the different depths z=z1 to zN.

In this operation mode, control of synchronization of the frame rate of the CCDs 21, 22 and 23, emission timing of the flash light, and movement timing of the reference mirror 8 are important.

Therefore, for example, a stepping motor is used as a driving device for the reference-mirror moving mechanism 8A. When the stepping motor is supplied with a pulse current as in a normal case, the shaft thereof is rotated by a specific rotation angle. A plurality of gears provided at a suitable gear ratio are interposed between the shaft of the stepping motor and the reference mirror 8, whereby a driving force for rotation at the specific angle of the shaft is converted into a specific movement distance of the reference mirror 8. The specific movement distance is set to a depth interval $\Delta z = |z(i+1) - zi|$ (i=1 to N−1).

The controller 31 intermittently supplies power to the xenon lamp 2 at the timing synchronized with the frame rate of the CCDs 21, 22 and 23 and intermittently supplies a pulse current to the stepping motor for the reference-mirror moving mechanism 8A. Consequently, the xenon lamp 2 intermittently emits the flash light at the timing synchronized with the frame rate. Then, the reference mirror 8 intermittently moves at the timing synchronized with the frame rate (i.e., z-scan).

In this operation mode, the process for forming an image of the measurement object O can be performed as in the above-mentioned operation mode.

In this operation mode, the interval Δz between the depths z=z1 to zN is constant. Even when the depth interval varies, this operation example can be applied. For example, the gear ratio between the shaft of the stepping motor and the reference mirror 8 is changed to reduce the movement distance of the reference mirror 8 with respect to the rotation angle of the shaft of the stepping motor. By supplying a specific number of pulse currents for each depth interval $\Delta z_i=|z(i+1)-z_i|$ ($z=1$ to $N-1$), it is possible to achieve a target movement distance $\Delta z_i$ of the reference mirror 8. In addition, it is also possible to achieve the movement distance $\Delta z_i$ with a configuration using an ultrasonic motor.

[Actions and Advantageous Effects]

According to the optical image measuring apparatus 1 of this embodiment as described above, the following actions and advantageous effects are obtained.

The optical image measuring apparatus 1 according to this embodiment acts as follows. First, the xenon lamp 2 and the optical filter 2A emit a broadband flash light. This flash light is converted into a linearly polarized light by the polarizing plate 3 and is split into the signal light S and the reference light R by the half mirror 6. The reference light R of the linearly polarized light is converted into a circularly polarized light by the wavelength plate 7. Then, (part of) the reference light R of the circularly polarized light having returned from the reference mirror 8 passes though the half mirror 6, and (part of) the signal light S of the linearly polarized light having returned from the measurement object O is reflected by the half mirror 6. As a result, the interference light L is generated.

At this moment, from the reference light R reflected by the half mirror 6 and the signal light S passed through the half mirror 6, interference light having the same characteristic as the interference light L is generated (as described earlier). This interference light is detected by the CCD 23.

The interference light L generated by the half mirror 6 is split into the S-polarization component L1 and the P-polarization component L2 by the polarization beam splitter 11. The S-polarization component L1 is detected by the CCD 21 and the P-polarization component L2 is detected by the CCD 22.

The signal processor 20 of the computer 30 forms an image of the measurement object O based on the three detection signals outputted from the CCDs 21, 22 and 23.

According to the optical image measuring apparatus 1 thus acting, it is possible to form an image of the measurement object O by using the result of the detection of the interference light generated from one flash light. Therefore, it is possible to form a highly accurate image without being influenced by movement of the measurement object O.

Furthermore, unlike in the conventional configuration using a light cutoff device (i.e., shutter) for generating a plurality of interference light pulses, an image is formed by using the polarization characteristic of the interference light. Therefore, there is a merit that it is unnecessary to perform complicated synchronization control between the light cutoff device and the light source.

According to this embodiment, the flash light is intermittently emitted in synchronization with the frame rate of the CCDs 21, 22 and 23, and the image is formed based on the result of detection of the interference light L generated from each flash light. Therefore, it is possible to smoothly perform continuous measurement on the measurement object O.

Further, since it is possible to changing the position of the reference mirror 8 to perform the z-scan while intermittently emitting the flash light, it is possible to smoothly measure the images of the measurement object O at different depths thereof.

Further, the apparatus is configured to monitor the amount of flash light emitted from the xenon lamp 2 and regulate the luminance of the image in accordance with the light amount value. Therefore, even if the xenon lamp 2 in which the amount of light varies at every emission of the light is used, it is possible to obtain images with (substantially) constant luminance. In particular, in a case where measurement of images is continuously performed for the measurement object O, the respective images have constant luminance. Therefore, there is a merit in that observation of the images becomes easier.

Further, the optical image measuring apparatus 1 splits the broadband light emitted from the xenon lamp 2 into the signal light S and the reference light R, and converts the polarization characteristic of the reference light R (into circular polarization). Furthermore, the optical image measuring apparatus 1 superimposes the reference light R whose polarization characteristic has been converted with the signal light S to generate the interference light L, and extracts the two polarization components (S-polarization component and P-polarization component) of the interference light L to detect by the CCDs 21 and 22, respectively. Then, based on the detection results and the result of the other detection by the CCD 23, the optical image measuring apparatus 1 forms an image of the measurement object O.

Thus, according to the optical image measuring apparatus 1, it is possible to simultaneously acquire the two polarization components of the interference light L, so that it is possible to shorten the measurement time.

Further, according to the optical image measuring apparatus 1, it is possible to simultaneously detect the two polarization components L1 and L2 of the interference light L, and there is no error in time for detection of the two polarization components L1 and L2. Therefore, it is possible to form a highly accurate image without an influence of the movement of the measurement object O. In a case where the two polarization components L1 and L2 are acquired non-simultaneously, a position of the measurement object O at the time of detection of the polarization component L1 and a position of the measurement object O at the time of detection of the polarization component L2 may be different from each other. Consequently, "flow" (i.e., unsharpness of an image on which misalignment of the measurement object O at the time of detection of the polarization components L1 and L2 is reflected) may occur in an image of the measurement object O. However, according to the optical image measuring apparatus 1, it is possible to reduce the risk of occurrence of the "flow."

[Modification]

In the above-mentioned embodiment, the beam splitter 12 is provided between the lens 5 and the half mirror 6, and the interference light guided by the beam splitter 12 is detected by the CCD 23 (third detector) to obtain the intensity of the background light. A modification related to the set position of the third detector for obtaining the intensity of the background light will be described below.

Figure 3:
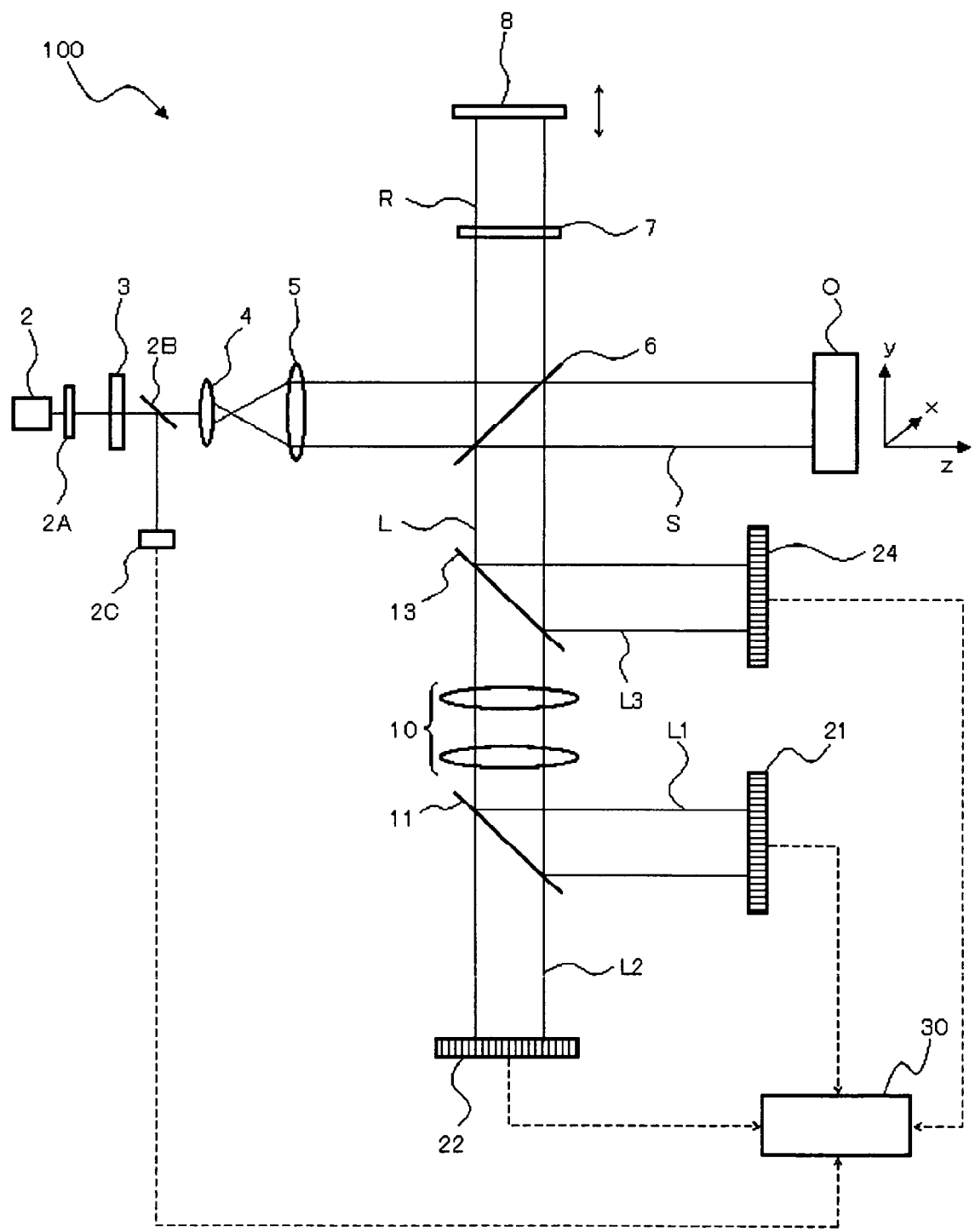
FIG. 3 is a schematic diagram showing an example of a configuration in a modification of the embodiment of the optical image measuring apparatus according to the present invention.

In an optical image measuring apparatus 100 shown in FIG. 3, a beam splitter 13 is obliquely provided on the optical path of the interference light L between the half mirror 6 and the imaging lens group 10. A CCD 24 is provided on an optical path L3 branched by the beam splitter 13. The CCD 24 corresponds to an example of the "third detector." The CCD 24 receives the interference light L reflected by the beam splitter 13 and outputs a detection signal (i.e., third detection signal) to the computer 30.

The optical image measuring apparatus 100 also enables formation of the image of the measurement object O as in the optical image measuring apparatus 1 according to the above-mentioned embodiment, and it is possible to obtain the same actions and advantageous effects.

[Other Modifications]

The configurations described in detail above are merely examples of the configuration for embodying the optical image measuring apparatus according to the present invention. Therefore, it is possible to make various modifications within the gist of the present invention.

First, an optical image measuring apparatus having an operational principle different from that in the above-mentioned embodiment will be described. The optical image measuring apparatus has the same configuration as shown in FIG. 1 or 3. However, the optical image measuring apparatus includes a light source for emitting measurement light composed of continuous light, instead of the xenon lamp 2 for emitting the flash light in the above-mentioned embodiment. A xenon lamp capable of continuously emitting light, an LED emitting a sufficiently large amount of light, or the like can be used for the light source. Moreover, it is also possible to use a thermal light source (halogen lamp) other than the xenon lamp. Thus, the light source can be any one that emits a broadband light. The optical filter 2A is a filter that transmits only light of a specific band of the broadband light emitted from the light source. For example, the optical filter 2A transmits light of a band whose central wavelength is about 760 nm and whose wavelength width is about 100 nm, of the broadband light emitted from the light source.

The CCDs 21 and 22 of the optical image measuring apparatus each change an exposure time (a light accumulation time) in accordance with a control signal from the computer 30. Control of the exposure time corresponds to a function normally called an "electronic shutter" or the like. The computer 30 (the controller 31 thereof: see FIG. 2) operates as an example of the "exposure-time changer" in the present invention.

The computer 30 sets the exposure time for each of the polarization components L1 and L2 detected by the CCDs 21 and 22 to a time shorter than the frame rate thereof, desirably, a time sufficiently shorter than the frame rate. According to the electronic shutter function, it is possible to minutely control the exposure time as compared with a mechanical shutter.

The computer 30 (the signal processor 20 thereof: see FIG. 2) forms an image by the same process as in the above-mentioned embodiment, based on the detection signals based on the polarization components L1 and L2 of the interference light L which are detected by the CCDs 21 and 22 and the detection signal based on the interference light detected by the CCD 23.

According to the optical image measuring apparatus having the above-mentioned configuration, it is possible to change the exposure time of each of the CCDs 21 and 22. Therefore, by setting the exposure time to a sufficiently short time, it becomes possible to form a highly accurate image without being influenced by the movement of the measurement object. The image is formed based on the polarization characteristic of the interference light in place of conventional mechanical light cutoff devices (i.e., shutters), so that there is a merit that it is unnecessary to perform complicated synchronization control.

The measurement light emitted from the light source of the optical image measuring apparatus may be pulse light. The pulse light has a shorter light emission time than the frame rate of the CCDs 21 and 22. The computer 30 sets the exposure time for each of the polarization components L1 and L2 detected by the CCDs 21 and 22 to a time shorter than the light emission time of the pulse light (a substantially equal time or a shorter time than the light emission time). With such a configuration, the same action and advantageous effects as those in the above-mentioned optical image measuring apparatus can be obtained.

Hereinafter, various modifications which can be applied to the optical image measuring apparatus according to the above-mentioned embodiment and the above-mentioned modification will be described. First, a wavelength plate (½-wavelength plate) is provided on the optical path of the signal light S, that is, between the half mirror 6 and the measurement object O in the configuration shown in FIG. 1 or 3, whereby it becomes possible to correct the tilt of the polarization direction of the signal light S which is caused by a change in phase when the signal light S propagates through the measurement object O.

In the above-mentioned embodiment etc., the polarization characteristic of the reference light R is converted into the circular polarization. However, it is also possible to position the wavelength plate 7 on the optical path of the signal light S to convert the polarization characteristic of the signal light S into the circular polarization.

The detector applicable to the optical image measuring apparatus according to the present invention is not limited to the CCD. It is possible to use any optical sensor such as a CMOS sensor that detects interference light using 2-dimensionally arranged pixels, performs photoelectric conversion and outputs a detection signal.

In the above-mentioned embodiment or the like, the optical image measuring apparatus including the Michelson type interferometer is described. However, it is also possible to employ another interferometer such as a Mach-Zehnder type interferometer (see, for example, Japanese Patent JP 3245135 made by the inventors of the present invention).

Further, by disposing an optical fiber (bundle) used as a light guide member in part of the interferometer, it is possible to increase the degree of freedom of an apparatus design, make the apparatus compact in size, or increase the degree of freedom of location of the measurement object (see, for example, JP 3245135 described above).

When the optical image measuring apparatus according to the present invention is applied to, for example, an ophthalmologic field, it is possible to acquire a 2-dimensional image of retina and cornea in addition to a blood flow state obtained by blood flow measurement on an eye fundus. Consequently, it is possible to measure, for example, the number of endothelial cells of the cornea. It is needless to say that various other applications are also possible.

Second Embodiment

[Configuration of Apparatus]

Figure 4:
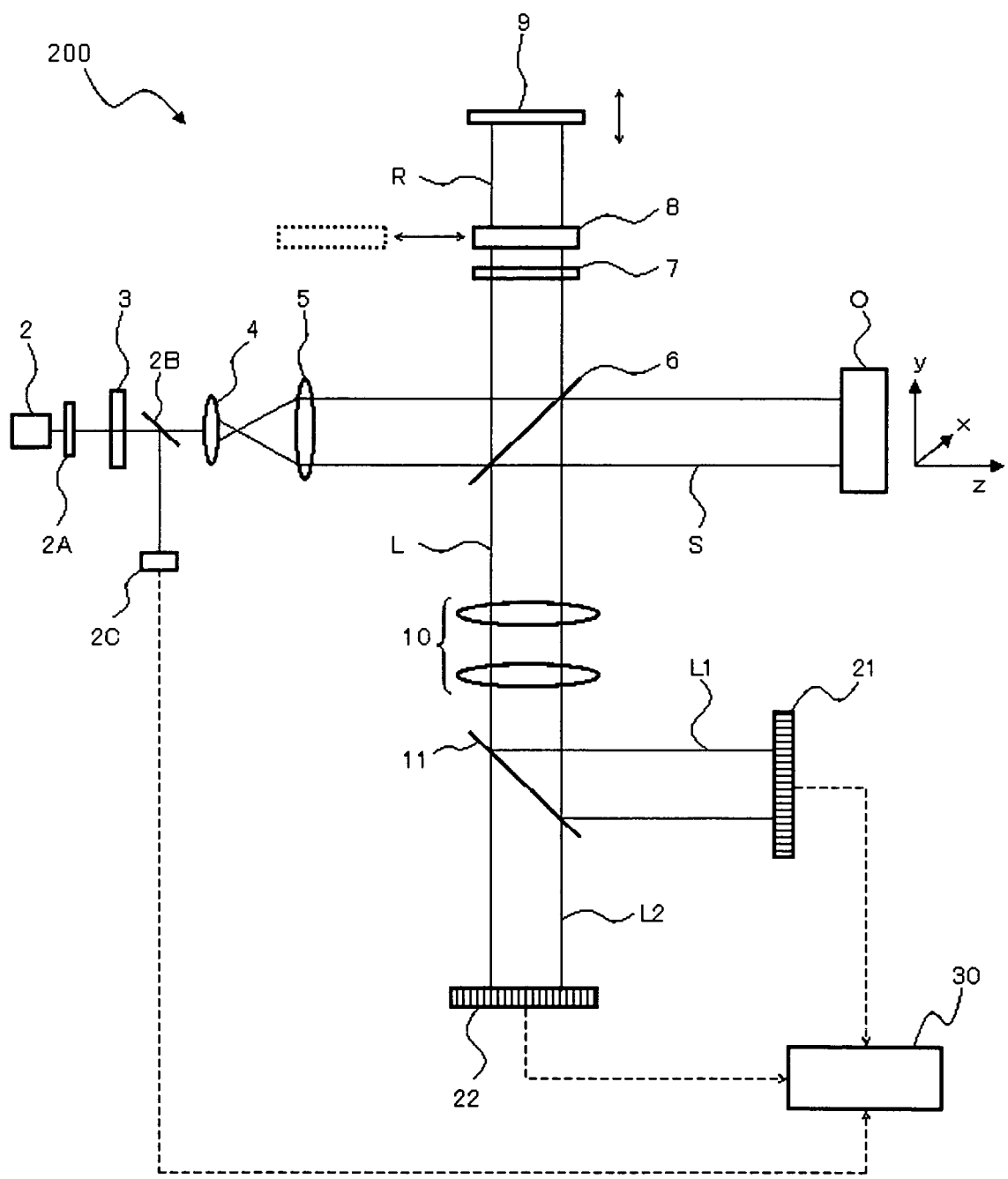
FIG. 4 is a schematic diagram showing an example of a configuration in an embodiment of the optical image measuring apparatus according to the present invention.

In the following descriptions, components similar to those in the first embodiment will be denoted by the same reference symbols. FIG. 4 shows an example of a schematic configuration in an embodiment of the optical image measuring apparatus according to the present invention. An optical image measuring apparatus 200 shown in FIG. 4 comprises the xenon lamp 2 configured to emit a flash light, and the optical filter 2A configured to convert the emitted flash light into a low-coherent broadband light. The xenon lamp 2 and the optical filter 2A correspond to an example of the "light-emitting part" configured to emit a broadband light in the present invention.

On the optical path of the flash light converted into the broadband light, the polarizing plate 3 configured to convert the polarization characteristic of the flash light to linear polarization, the beam splitter 2B, the lenses 4 and 5 configured to increase the diameter of the flash light and convert to a parallel light, the beam splitter 12, and the half mirror 6 are provided.

The flash light is split into the signal light S heading to the measurement object O and the reference light R heading to the reference mirror 8 by the half mirror 6. On the optical path of the reference light R, the wavelength plate 7, an opticalpath-length changing optical element 9 and the reference mirror 8 are provided. Hereinafter, these members will be described in detail.

The xenon lamp 2 acts to emit the flash light as in a normal case, and corresponds to an example of the "light source" in the present invention. The xenon lamp 2 emits a sufficiently large amount of light as compared with an SLD used in a conventional optical image measuring apparatus. As the "light source" in the present invention, it is possible to apply any light source, such as an LED, that emits a sufficiently large amount of light as compared with an SLD.

The optical filter 2A is positioned on the optical path of the flash light emitted from the xenon lamp 2, and acts to convert the flash light into the low-coherent broadband light as described above.

In an xyz-coordinate system shown in FIG. 4, an advancing direction of the signal light S (flash light) is defined as a z-axis direction, and an oscillation plane of the signal light S that is orthogonal to the advancing direction is defined as an x-y plane. An x-axis direction and a y-axis direction are defined so as to coincide with an oscillation plane of an electric field component of the signal light S and an oscillation plane of a magnetic field component thereof, respectively.

The polarizing plate 3 is a polarization conversion element configured to transmit the oscillation component of a specific direction of the flash light emitted from the broadband light source 2. The polarizing plate 3 in this embodiment is configured to transmit the oscillation component of an angle direction forming an angle of 45° with the x-axis (and the y-axis) of the x-y plane. Consequently, the flash light having transmitted through the polarizing plate 3 has linear polarization of 45°. That is, polarization components in the x-axis direction of the flash light and polarization components in the y-axis direction have equal amplitudes. In other words, a P-polarization component and an S-polarization component of the flash light have equal amplitudes.

The half mirror 6 acts to split the flash light into the signal light S heading to the measurement object O and the reference light R heading to the reference mirror 8, and corresponds to an example of the "splitter" in present invention. The half mirror 6 transmits part (half) of the flash light to obtain the signal light S and reflects the rest thereof to obtain the reference light R.

Further, the half mirror 6 also acts as an example of the "superimposing part" in the present invention, configured to superimpose the signal light S returning from the measurement object O and the reference light R returning from the reference mirror 8 to generate the interference light L.

In this embodiment, about the half mirror 6 obliquely disposed on the optical path of the flash light emitted from the xenon lamp 2, the measurement object O is disposed on an extension of the optical path of the flash light, and the reference mirror 8 is disposed in a direction orthogonal to the optical path of the flash light, whereby a Michelson interferometer is formed. Therefore, in this embodiment, the "splitter" and the "superimposing part" are configured by (different reflection faces of) the half mirror 6.

In a case where another type of interferometer such as a Mach-Zehnder interferometer is applied, the "splitter" and the "superimposing part" may be configured by separate optical elements.

Further, as the "splitter" and the "superimposing part", it is possible to apply any non-polarization beam splitter having no effect on the polarization characteristics of the flash light, the signal light S and the reference light R.

The wavelength plate 7 corresponds to an example of "converter" in the present invention, and is a polarization conversion element configured to convert the polarization characteristic of the reference light R having linear polarization. In this embodiment, as the wavelength plate 7, a ⅛-wavelength plate that acts to apply a phase difference of $\pi/4$ to between a P-polarization component and an S-polarization component of light passing through the wavelength plate is used.

The reference light R passes through the wavelength plate 7 when heading from the half mirror 6 to the reference mirror 8 and when being reflected by the reference mirror 8 and heading to the half mirror 6, respectively. As a result, a phase difference of $\pi/2$ is applied to the reference light R having been reflected by the reference mirror 8 and having returned to the half mirror 6. Therefore, as in the case where a ¼-wavelength plate acts on the reference light R initially having linear polarization of light of 45°, the polarization characteristic of the reference light R having returned to the half mirror 6 is circular polarization. When another interferometer such as the Mach-Zehnder interferometer in which reference light passes through the wavelength plate only one time is used, the ¼-wavelength plate is applied as the "converter."

The optical-path-length changing optical element 9 is an optical element configured to change the optical path length of the reference light R by a specific distance, and is made of a material such as glass. The optical-path-length changing optical element 9 is configured to be inserted into and removed from the optical path of the reference light R by a mechanism described later. The optical-path-length changing optical element 9 corresponds to an example of the "optical-path-length changing member" in the present invention.

The reference mirror 8 corresponds to an example of the "reference object" in the present invention, and has a reflection face orthogonal to the optical path direction (advancing direction) of the reference light R. The reference mirror 8 is moved in the optical path direction of the reference light R by a mechanism described later. Consequently, it becomes possible to extract a component reflected in a target depth region from reflected light of the signal light S in various depth (z-coordinate) regions of the measurement object O. The phase of the reference light R is shifted by movement of the reference mirror 8.

The extraction of the reflected component in the target depth region will be more specifically described. Since the signal light S and the reference light R are each a low-coherent light, only a portion of the signal light S propagating a distance substantially equal to that of the reference light R contributes to generation of the interference light L. In other words, only a reflected light in a depth region of the measurement object O that is located at a distance substantially equal to an optical path length to the reference mirror 8 interferes with the reference light R to generate the interference light L. Therefore, by moving the reference mirror 8 and changing the optical path length of the reference light R (performing z-scan), it is possible to subsequently extract the reflected light in various depth regions of the measurement object O.

The optical image measuring apparatus 200 further comprises the imaging lens group 10 configured to image the interference light L generated by the half mirror 6 serving as the superimposing part, the polarization beam splitter 11 configured to split the optical path of the interference light L based on the polarization characteristics, and the CCD image sensors (merely referred to as CCDs) 21 and 22 provided on the respective optical paths of the split interference light L. Each of the CCDs 21 and 22 outputs a detection signal corresponding to detected light to a computer 30.

The polarization beam splitter 11 acts to extract a plurality of different polarization components from the interference light L, and corresponds to an example of the "extracting part" in the present invention. To be more specific, the polarization beam splitter 11 acts to reflect an S-polarization component L1 of the interference light L and make the S-polarization component L1 enter the CCD 21, and also acts to transmit a P-polarization component L2 thereof to make the P-polarization component L2 enter the CCD 22. The S-polarization component L1 and the P-polarization component L2 of the interference light L have equal amplitudes (i.e., maximum intensities).

The CCD 21 detects the S-polarization component L1 of the interference light L extracted by the polarization beam splitter 11, performs photoelectric conversion to generate a detection signal, and outputs the detection signal to the computer 30. Similarly, the CCD 22 detects the extracted P-polarization component L2 of the interference light L, performs photoelectric conversion to generate a detection signal, and outputs the detection signal to the computer 30. The CCDs 21 and 22 correspond to examples of the "first detector" and the "second detector," respectively, in the present invention. The detection signals outputted from the CCDs 21 and 22 correspond to examples of the "first detection signal" and the "second detection signal," respectively.

The CCDs 21 and 22 is capable of detecting light at a specific frame rate such as 30 frames per second, and outputting detection signals.

The photodetector 2C detects part (i.e., light reflected by the beam splitter 2B) of the flash light emitted from the xenon lamp 2 and converted into the broadband light, performs photoelectric conversion to generate a detection signal, and outputs the detection signal to the computer 30. The detection signal has a signal intensity corresponding to the amount (intensity) of the detected flash light. The photodetector 2C corresponds to an example of the "light-amount detector" in the present invention.

[Configuration of Control System]

Figure 5:
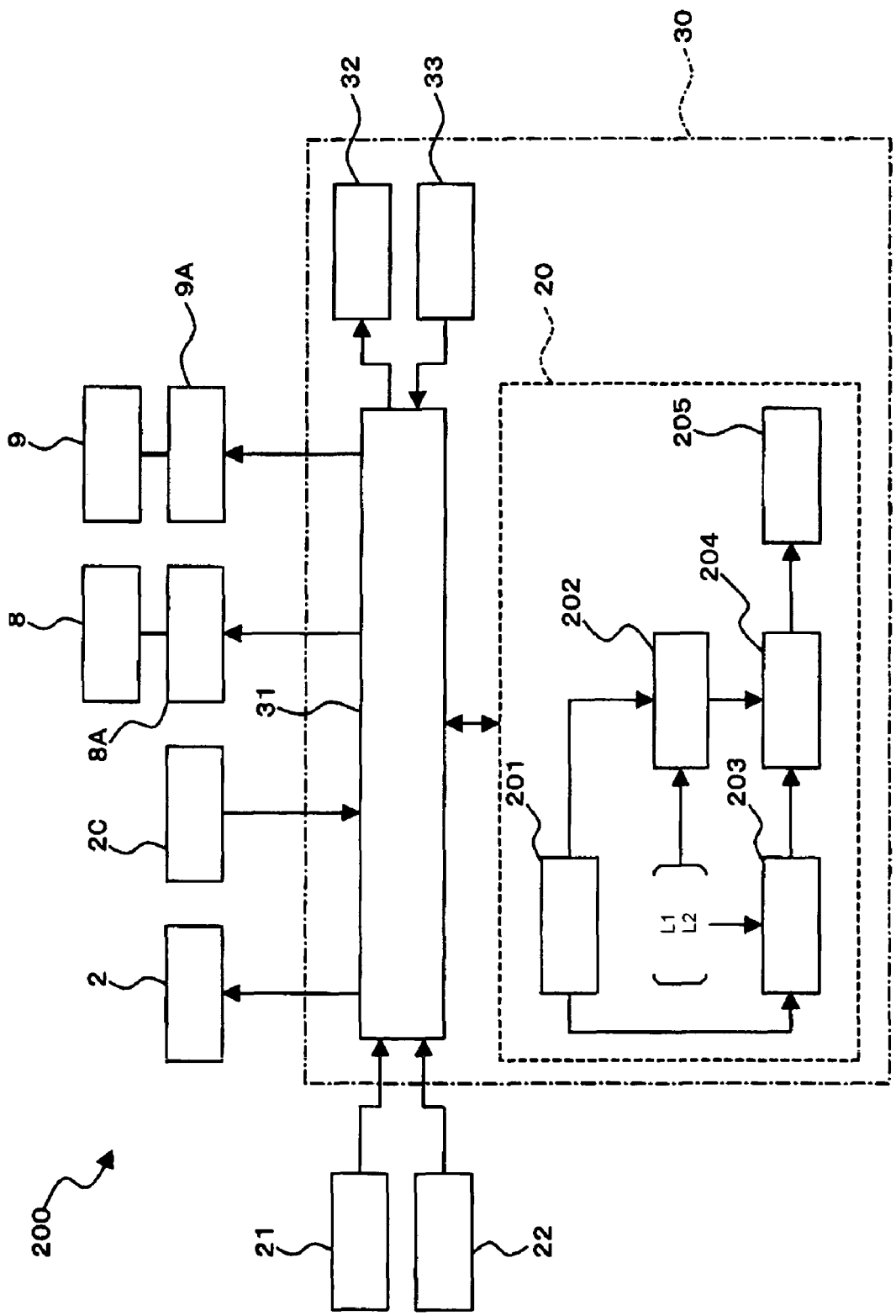
FIG. 5 is a schematic block diagram showing an example of a configuration of a control system in the embodiment of the optical image measuring apparatus according to the present invention.

FIG. 5 shows an example of a configuration of a control system of the optical image measuring apparatus 200. The optical image measuring apparatus 200 is provided with the computer 30.

As in the general case, the computer 30 includes a microprocessor such as a CPU, a RAM, a ROM, and a hard disk drive. Specific control programs, calculation programs and data such as various parameters are stored in advance in the hard disk drive. The microprocessor loads the programs and data on the RAM and executes various control processes and calculation processes. The computer 30 includes the signal processor 20, the controller 31, the display 32, and the operation part 33.

The controller 31 controls the respective parts of the optical image measuring apparatus 200 and includes a microprocessor, a RAM, a ROM, a hard disk drive, and a power source circuit. The controller 31 performs, for example, control for power supply to the xenon lamp 2, control for operation of an optical element insertion and removal mechanism 9A, control for operation of a reference-mirror moving mechanism 8A, control for making the display 32 display various screens and images, and control for operation of the apparatus based on operation signals from the operation part 33. The controller 31 corresponds to an example of the "controller" in the present invention.

The optical element insertion and removal mechanism 9A is a mechanism configured to insert and remove the optical-path-length changing optical element 9 into and from the optical path of the reference light R. The optical element insertion and removal mechanism 9A is composed of, for example, a driving device such as a solenoid that linearly moves the optical-path-length changing optical element 9, or, a rotation drive mechanism that rotates a turret plate for holding the optical-path-length changing optical element 9, or the like.

In this embodiment, in a state where the optical-path-length changing optical element 9 is retracted from the optical path of the reference light R, the signal light S and the reference light R are superimposed and the interference light L is generated. In a state where the optical-path-length changing optical element 9 is inserted into the optical path, the signal light S and the reference light R does not interfere with each other because the optical path length is changed (because a low-coherent light is used).

The reference-mirror moving mechanism 8A is a mechanism configured to move the reference mirror 8 in the optical path direction of the reference light R in order to perform z-scan of the measurement object O. The reference-mirror moving mechanism 8A may be a mechanism that continuously moves the reference mirror 8, or may be a mechanism that intermittently moves the reference mirror 8. In a case where the reference mirror 8 is continuously moved, the reference-mirror moving mechanism 8A includes a driving device such as a normal motor and an ultrasonic motor, and a mechanism such as various kinds of gears and shafts for transferring a driving force to the reference mirror 8. In a case where the reference mirror 8 is intermittently moved, the reference-mirror moving mechanism 8A includes a driving device such as a stepping motor and an ultrasonic motor, and a mechanism for transferring a driving force to the reference mirror 8.

To the controller 31, the detection signals outputted from the CCDs 21 and 22 and the detection signal outputted from the photodetector 2C are inputted.

The display 32 is composed of any display device such as a liquid crystal display (LCD) and a CRT display. The operation part 33 is composed of any operating device or input device, such as a mouse, a keyboard, a trackball, a joystick and a control panel. In a case where a touch panel type display, a pen tablet or the like is used, the display 32 and the operation part 33 are integrally formed.

The signal processor 20 corresponds to an example of the "image formation processor" in the present invention. The signal processor 20 executes a process for forming an image based on the detection signals from the CCDs 21 and 22, and includes a microprocessor, a RAM, a ROM, a hard disk drive, etc. The signal processor 20 includes the background-light calculator 201, the interference component intensity calculator 202, the phase-distribution calculator 203, the image forming part 204, and the image regulation processor 205.

The background-light calculator 201 calculates the background light component of the interference light L, based on the detection signal outputted from the CCD 21 (or the CCD 22), in a state where the optical-path-length changing optical element 9 is inserted into the optical path of the reference light R. The detection signal corresponds to an example of the "fourth detection signal" in the present invention.

In measurement of the background light component of the interference light L, the optical-path-length changing optical element 9 is inserted into the optical path of the reference light R. When flash light is emitted from the xenon lamp 2 in this state, the flash light is detected by the CCD 21 without generating interference light. The CCD 21 outputs the detection signal to the computer 30.

For example, the background-light calculator 201 integrates the detection signal for one wavelength (or an integral multiple thereof) to cancel an interference component of the detection signal and extract a DC component thereof. Since the xenon lamp 2 identical to that used for generation of the interference light L is used, the extracted DC component is considered to be substantially identical to the background light component of the interference light L. Therefore, both the components will be identified with each other.

The background light component of the interference light L obtained by the background-light calculator 201 is inputted to the interference component intensity calculator 202. The background-light calculator 201 thus acting corresponds to an example of the "background-light calculator" in the present invention.

By monitoring the amount of the light emitted from the xenon lamp 2, it is possible to make the background light component calculated by the background-light calculator 201 closer to the actual background light component of the interference light L. For example, the amount of a flash light for measuring the background light component and the amount of a flash light for measuring the interference light L are obtained by using the photodetector 2C. Then, the value of the background light component is corrected based on the ratio of these light amount values (i.e., the same process as that performed by the image regulation processor 205 described later in detail is executed). Consequently, it is possible to obtain a value close to the background light component of the interference light L.

The interference component intensity calculator 202 calculates the signal intensities of interference components (phase quadrature components) of the S-polarization component L1 and the P-polarization component L2, respectively, based on the background light component (DC component) of the interference light L inputted from the background-light calculator 201, the detection signal based on the S-polarization component L1 of the interference light L inputted from the CCD 21, and the detection signal based on the P-polarization component L2 of the interference light L inputted from the CCD 22.

To be specific, first, the interference component intensity calculator 202 subtracts the background light component from the detection signal based on the S-polarization component L1, thereby obtaining the interference component of the S-polarization component L1. Similarly, the interference component intensity calculator 202 subtracts the background light component from the detection signal based on the P-polarization component L2, thereby obtaining the interference component of the P-polarization component L2. Since the interference component of the S-polarization component L1 and the interference component of the P-polarization component L2 are phase quadrature components, one of the interference components is a cosine wave while the other is a sine wave, and the interference components have the same phase.

The interference component intensity calculator 202 calculates the square sum of the two interference components, and calculates the square root of the value of the square sum, thereby obtaining the amplitude (signal intensity) of the interference components of the S-polarization component L1 and the P-polarization component L2, and the amplitude of the interference light L. The obtained signal intensity is inputted to the image forming part 204. The interference component intensity calculator 202 thus acting corresponds to an example of the "interference component intensity calculator" in the present invention.

The phase-distribution calculator 203 calculates a spatial distribution of phases of the interference light, based on the background light component of the interference light L inputted from the background-light calculator 201, the detection signal based on the S-polarization component L1 of the interference light L inputted from the CCD 21, and the detection signal based on the P-polarization component L2 thereof inputted from the CCD 22.

To be more specific, first, the phase-distribution calculator 203 calculates a ratio of the interference component of the S-polarization component L1 and the interference component of the P-polarization component L2, which are the cosine wave and the sine wave having the same phase, to obtain a tangent function. Since the amplitude of the S-polarization component L1 is equal to that of the P-polarization component L2, the tangent function does not depend on the amplitude of the interference light L (cancelled between numerator and denominator). The tangent function includes only phase information. The phase-distribution calculator 203 calculates an inverse function of the tangent function, thereby obtaining the phase information. The obtained phase information is outputted to the image forming part 204.

In view of the fact that a plurality of light receiving elements (pixels) are 2-dimensionally arranged on the light receiving faces of the CCDs 21 and 22, the phase information obtained by the phase-distribution calculator 203 presents a phase distribution state in a 2-dimensional coordinate plane defined on each of the light receiving faces of the CCDs 21 and 22. The phase-distribution calculator 203 thus acting corresponds to an example of the "phase-distribution calculator" in the present invention.

The image forming part 204 executes a process for forming an image of the measurement object O, based on the signal intensities of the interference components of the S-polarization component L1 and the P-polarization component L2 of the interference light L inputted from the interference component intensity calculator 202. Moreover, the image forming part 204 forms an image presenting the spatial distribution of phases of the interference light L, based on the phase information inputted from the phase-distribution calculator 203.

The signal intensities of the interference components of the S-polarization component L1 and P-polarization component L2 of the interference light L inputted from the interference component intensity calculator 202 are obtained for each pixel on the light receiving faces of the CCDs 21 and 22. The image forming part 204 designates a brightness value corresponding to the signal intensity of the interference component of the polarization component for each pixel, thereby forming a tomographic image presenting the morphology of the measurement object O at a specific depth (z-coordinate value). The tomographic image is a monochrome contrast image. It is also possible to form a color image by designating a red (R) value, a green (G) value and a blue (B) value corresponding to the signal intensity of the interference component of the polarization component.

Next, a process for forming an image presenting the spatial phase distribution will be described. Since the interference light L is generated based on the flash light from the xenon lamp 2, the phase information obtained by the phase-distribution calculator 203 is an instantaneous phase value. Therefore, it is considered that the phase information is constant without depending on a pixel position of the CCDs 21 and 22.

In view of this assumption, for example, the image forming part 204 obtains a difference in phase of detection signals at the respective pixels, with reference to a phase value detected at a pixel located in a specific point on the light receiving faces of the CCDs 21 and 22. Brightness (i.e., reference brightness) of the reference phase value is designated, and a brightness value of each pixel is designated according to the obtained phase difference. Consequently, an image expressing a spatial distribution of the phase difference of the interference light L is formed.

The image regulation processor 205 acts to regulate the luminance of the image formed by the image forming part 204, based on the amount of the flash light detected by the photodetector 2C. Here, the term "luminance" means brightness in the case of a monochrome image, and brightness or lightness (i.e., maximum value of brightness of R, G and B) in the case of a color image. An image whose luminance is regulated is an image formed to which the signal intensity (i.e., amplitude) of the interference light L is reflected. (Therefore, the image presenting the spatial phase distribution is excepted.)

The amount of the flash light emitted from the xenon lamp 2 varies every time the light is emitted. The image regulation processor 205 regulates the luminance of the image based on the amount of flash light emitted at the time of image measurement, thereby obtaining an image whose luminance is maintained at a constant level. Such an action of the image regulation processor 205 is particularly effective in the case where a plurality of images are obtained for the measurement object O.

Upon receiving the image formed by the image forming part 204, the image regulation processor 205 uses the light amount value detected by the photodetector 2C at the time of image measurement, and thereby corrects the brightness value or lightness value of each pixel composing the image.

A specific example of this method will be described. First, a reference light amount value Q0 of the flash light is set in advance. When the light amount detected by the photodetector 2C is Q, the image regulation processor 205 corrects the brightness value (or the lightness value) $L(x, y)$ of each pixel of the image formed by the image forming part 204 to $(Q0/Q) \times L(x, y)$.

Consequently, even when the light amount Q gets larger than the reference light amount value Q0, and thus, the image becomes brighter than the reference, or even when the light amount Q gets smaller than the reference light amount value Q0, and thus, the image becomes darker than the reference, it is possible to obtain an image whose luminance is substantially equal to that in the case of measurement using the reference light amount value. Such a method can be applied even when only an image is formed, or even when a plurality of images are formed.

As another specific example of the regulation process of luminance of an image, it is possible to use the following method, in the case of forming a plurality of images (for example, at different depths) are formed for the measurement object O. When N-sheets images are obtained for the measurement object O, for example, a light amount value of flash light detected at the time of measurement of an ith image is set as a reference light amount value Qi (i=any one of 1 to N). Then, a detection light amount value obtained at the time of measurement of a jth (j=1 to N, j≠i) image is expressed by Qj. In this case, the image regulation processor 205 corrects a brightness value (or lightness value) $Lj(x, y)$ of each pixel of the jth image to $(Qi/Qj) \times Lj(x, y)$. Consequently, the luminance of each of the N-images can be made substantially equal to the luminance of the ith image.

It is also possible to compare the brightness values (or lightness values) at a specific pixel in a plurality of images, and set the average value, for example, thereof as a reference light amount value, thereby regulating the luminance of each of the images.

[Operation Mode]

An operation mode of the optical image measuring apparatus 200 in this embodiment configured as described above will be described. Hereinafter, an operation example in the case of forming the N-sheets of images G1 to GN corresponding to the depths z=z1 to zN of the measurement object O will be described.

First, the background light component is measured. For this, the controller 31 controls the optical element insertion and removal mechanism 9A to insert the optical-path-length changing optical element 9 into the optical path of the reference light R, and controls the reference-mirror moving mechanism 8A to move the reference mirror 8 to an initial position for measurement (a position corresponding to z=z1). Then, the controller 31 supplies power to the xenon lamp 2 so as to emit a flash light. The CCD 21 detects the flash light and outputs a detection signal to the computer 30. At this moment, if necessary, the photodetector 2C detects the amount of the flash light and outputs a detection signal to the computer 30.

The background-light calculator 201 obtains the background light component based on the detection signal from the CCD 21.

Next, the controller 31 controls the optical element insertion and removal mechanism 9A so that the optical-path-length changing optical element 9 retracts from the optical path of the reference light R. Then, the controller 31 controls the xenon lamp 2 so as to emit a flash light for forming a first image, and controls the reference-mirror moving mechanism 8A to start continuous movement of the reference mirror 8 at a constant speed.

The flash light is converted into a low-coherent broadband light by the optical filter 2A, and the polarization characteristic thereof is converted to linear polarization by the polarizing plate 3. Part of the light is reflected by the beam splitter 2B and the amount of the light is detected by the photodetector 2C. The detected light amount value is sent to the computer 30 and stored in (the RAM or the hard disk drive of) the controller 31.

The flash light having transmitted through the beam splitter 2B is increased in diameter and converted into a parallel light by the lenses 4 and 5. Then, the light heads to the half mirror 6.

The half mirror 6 splits the flash light into the signal light S and the reference light R. The signal light S advances toward the measurement object O. Then, the signal light S is reflected at various depth positions of the measurement object O, and returns to the half mirror 6. While the reference light R reciprocates between the half mirror 6 and the reference mirror 8, the polarization characteristic thereof is converted to circular polarization by the wavelength plate 7.

The half mirror 6 superimposes the signal light S having returned from the measurement object O and the circularly polarized reference light R having returned from the reference mirror 8 to generate the interference light L. Because the signal light S and the reference light R are low-coherent, the interference light L includes information at a depth position (z=z1) of the measurement object O that is substantially equal to a distance between the half mirror 6 and (the reflection face of) the reference mirror 8 at the time when the reference light R is reflected on the reference mirror 8. (In other words, the interference light L includes information on a depth position corresponding to a width of about a coherence length of a broadband light.)

The interference light L is converted from a parallel light into a focused light by the imaging lens group 10, and split into the S-polarization component L1 and the P-polarization component L2 by the polarization beam splitter 11. The S-polarization component L1 is detected by the CCD 21, and the P-polarization component L2 is detected by the CCD 22. The CCDs 21 and 22 transmit detection signals to the computer 30, respectively.

The controller 31 sends the first detection signals from the CCDs 21 and 22, and the detection signal from the photodetector 2C, to the signal processor 20. Moreover, when a specific time elapses after emission of the flash light for the first image measurement, the controller 31 causes the xenon lamp 2 to emit a flash light for second image measurement. Before emission of the flash light for the second image measurement, the reference mirror 8 is moved to a position corresponding to the depth z=z2. The second image measurement is performed as in the first image measurement. Timing for emission of the flash light is synchronized with the frame rate (for example, 30 frames per second) of the CCDs 21 and 22 by the controller 31.

Hereinafter, the operation of the signal processor 20 for forming the first image will be described. If necessary, the background-light calculator 201 corrects the value of the background light component having been obtained previously, based on the amount of the flash light at the time of measurement of the background light component and the amount of the flash light at the time of measurement of the interference light L. The interference component intensity calculator 202 calculates the signal intensity of the interference component of the S-polarization component L1 and the signal intensity of the interference component of the P-polarization component L2, based on the background light component calculated by the background-light calculator 201, the detection signal corresponding to the S-polarization component L1 from the CCD 21, and the detection signal corresponding to the P-polarization component L2 from the CCD 22. Next, the image forming part 204 forms the image G1 of the measurement object O at the depth z=z1, based on the signal intensities of the interference components of the S-polarization component L1 and the P-polarization component L2.

On the other hand, the phase-distribution calculator 203 calculates the spatial distribution of phases of the interference light L at the depth z=z1 of the measurement object O, based on the detection signals from CCDs 21 and 22. The image forming part 204 forms an image P1 presenting the spatial distribution of the phases of the interference light L.

As a result of execution of the above-mentioned process for each of the depths z=z1 to zN, the N-sheets of images G1 to GN and N-sheets of images P1 to PN are formed. Moreover, in the controller 31, light amount values Q1 to QN of the flash light at the time of measurement of the respective images G1 to GN are stored. The respective light amount values Q1 to QN are stored in association with the corresponding images G1 to GN.

A light amount value Qi of the flash light detected at the time of measurement of any image Gi of the N-sheets of images G1 to GN is set as a reference light amount value. The image Gi to become a reference may be selected by a user, or may be automatically selected. In an example of the automatic selection, it is possible to compare the brightness values (lightness values) of the images G1 to GN at a specific pixel, and set an image having an intermediate brightness value as the reference image. The selection process is performed by, for example, the controller 31.

Assuming the light amount value detected at the time of measurement of a jth image Gj is denoted by Qj (j=1 to N, j≠i), the image regulation processor 205 corrects the brightness value (or lightness value) Lj(x, y) of each pixel of the image Gj to (Qi/Qj)×Lj(x, y). Consequently, it is possible to make the luminance of each of the N-sheets of images G1 to GN substantially equal to the luminance of the ith image Gi for reference.

The images G1 to GN thus formed are stored in, for example, the hard disk drive of the controller 31. In a case where a storage device such as an image database is connected to the computer 30, it is possible to store the images G1 to GN in the storage device. In a case where the computer 30 is connected with a network such as a local area network (LAN), the images G1 to GN may be stored in (a database of) a server on the network.

[Another Operation Mode]

According to the above-mentioned operation mode, while the reference mirror 8 is continuously moved at a uniform speed to perform z-scan, the flash light is emitted at a timing synchronized with the frame rate of the CCDs 21 and 22, whereby the plurality of images G1 to GN of the measurement object O at the different depths z=z1 to zN are formed.

In contrast to this, according to an operation mode described below, while the reference mirror 8 is intermittently moved to perform z-scan, the flash light is emitted at a timing synchronized with the frame rate of the CCDs 21 and 22, whereby the plurality of images G1 to GN of the measurement object O at the different depths z=z1 to zN are formed.

In this operation mode, the synchronous control among the frame rate of the CCDs 21 and 22, the emission timing of the flash light, and the movement timing of the reference mirror 8 are important.

Thus, for example, a stepping motor is used as the driving device for the reference-mirror moving mechanism 8A. When a pulse current is supplied to the stepping motor as in a normal case, the shaft thereof is rotated by a specific rotation angle. A plurality of gears configured at a suitable gear ratio are interposed between the shaft of the stepping motor and the reference mirror 8 to convert a shaft driving force corresponding to the specific rotation angle into a specific movement distance of the reference mirror 8. The specific movement distance is set to a depth interval $\Delta z$ $(=|z(i+1)-zi|$ (i=1 to N−1).

The controller 31 intermittently supplies power to the xenon lamp 2 at the timing synchronized with the frame rate of the CCDs 21 and 22, and also intermittently supplies a pulse current to the stepping motor for the reference-mirror moving mechanism 8A. Consequently, the xenon lamp 2 intermittently emits a flash light at the timing synchronized with the frame rate. Then, the reference mirror 8 intermittently moves at the timing synchronized with the frame rate (i.e., z-scan).

The process for forming an image of the measurement object O in this operation mode can be performed as in the above-mentioned operation mode.

In this operation mode, the case where an interval $\Delta z$ between the respective depths z=z1 to zN is equal is described. Even when the depth intervals are different from one another, the operation example can be applied. For example, the gear ratio between the shaft of the stepping motor and the reference mirror 8 is changed, and the movement distance of the reference mirror 8 with respect to the rotation angle of the shaft of the stepping motor. By supplying a specific number of pulse currents for each depth interval $\Delta zi(=|z(i+1)-zi|$ (z=1 to N−1), it is possible to realize a target movement distance $\Delta zi$ of the reference mirror 8. In addition, it is also possible to realize the movement distance $\Delta zi$ with a configuration using an ultrasonic motor.

[Actions and Advantageous Effect]

According to the optical image measuring apparatus 200 in this embodiment, the following actions and advantageous effects are obtained.

The optical image measuring apparatus 200 in this embodiment acts in the following manner. First, the xenon lamp 2 emits a flash light, and then, the CCD 21 (or the CCD 22) detects the flash light and outputs a detection signal for calculating a background light component to the computer 30. Subsequently, the xenon lamp 2 emits a flash light again, and then, the optical filter 2A converts the flash light into a broadband light. This broadband flash light is converted into a linear polarized light by the polarizing late 3, and is split into the signal light S and the reference light R by the half mirror 6. The linearly polarized reference light R is converted into a circularly polarized light by the wavelength plate 7. (Part of) the circularly polarized reference light R having returned from the reference mirror 8 passes though the half mirror 6. (Part of) the linearly polarized signal light S having returned from the measurement object O is reflected by the half mirror 6. As a result, the interference light L is generated.

This interference light L is split into the S-polarization component L1 and the P-polarization component L2 by the polarization beam splitter 11. The S-polarization component L1 is detected by the CCD 21, and the P-polarization component L2 is detected by the CCD 22.

The signal processor 20 of the computer 30 forms an image of the measurement object O, based on the detection signal previously outputted from the CCD 21, and the detection signals corresponding to the S-polarization component L1 and the P-polarization component L2 outputted from the CCDs 21 and 22.

According to the optical image measuring apparatus 200 thus acting, it is possible to form an image of the measurement object O, based on the result of detection of the interference light generated from one flash light and the background light component measured additionally. Therefore, it is possible to form a highly accurate image without an influence of movement of the measurement object O.

Further, unlike a conventional configuration using a light cutoff device (a shutter) for generating a plurality of interference light pulses, the optical image measuring apparatus 200 forms an image by using the polarization characteristic of the interference light. Therefore, there is a merit that it is unnecessary to perform complicated synchronization control between the light cutoff device and the light source.

Furthermore, according to this embodiment, the optical image measuring apparatus 200 is configured to intermittently emit a flash light in synchronization with the frame rate of the CCDs 21 and 22, and form an image based on the result of detection of the interference light L generated from the respective flash lights. Therefore, it is possible to smoothly perform continuous measurement on the measurement object O.

Still further, it is possible to, while intermittently emitting a flash light, move the reference mirror 8 to perform z-scan. Therefore, it is possible to smoothly measure images of the measurement object O at different depths.

Still further, the optical image measuring apparatus 200 is configured to monitor the amount of a flash light emitted from the xenon lamp 2 and regulate the luminance of an image in accordance with the light amount value. Therefore, even when using the xenon lamp 2 in which the amount of light varies at every emission of light, it is possible to acquire images with (substantially) constant luminance. In particular, when continuous measurement of images of the measurement object O is performed, the respective images have substantially equal luminance. Therefore, there is a merit that image observation is facilitated.

Still further, the optical image measuring apparatus 200 splits the broadband light emitted from the xenon lamp 2 into the signal light S and the reference light R, and converts the polarization characteristic of the reference light R (into circular polarization). Furthermore, the optical image measuring apparatus 200 superimposes the reference light R with converted polarization characteristic with the signal light S to generate the interference light L, and extracts the two polarization components (S-polarization component and P-polarization component) of the interference light L to detect by the CCDs 21 and 22, respectively. The optical image measuring apparatus 200 executes this detection process in a state where the optical-path-length changing optical element 9 is inserted into an optical path of the reference light R and in a state where the optical-path-length changing optical element 9 is retracted from the optical path. Then, based on the results of the two detections, the optical image measuring apparatus 200 forms an image of the measurement object O.

Thus, according to the optical image measuring apparatus 200, it is possible to simultaneously acquire the two polarization components of the interference light L, so that it is possible to shorten the measurement time.

Further, according to the optical image measuring apparatus 200, it is possible to simultaneously detect the two polarization components L1 and L2 of the interference light L, and there is no error in time for detection of the two polarization components L1 and L2. Therefore, it is possible to form a highly accurate image without an influence of the movement of the measurement object O.

[Modification]

The configurations described in detail above are merely structural examples for embodying the optical image measuring apparatus according to the present invention. Therefore, various modifications can be made within the scope of the present invention.

First, an optical image measuring apparatus having an operational principle different from that in the above-mentioned embodiment will be described. The optical image measuring apparatus has the same configuration shown in FIG. 4. However, the optical image measuring apparatus includes a light source configured to emit a measurement light composed of a continuous light, instead of the xenon lamp 2 configured to emit the flash light in the above-mentioned embodiment. A xenon lamp capable of continuously emitting light, an LED emitting a sufficiently large amount of light, or the like can be used for the light source. Moreover, it is also possible to use a thermal light source (halogen lamp) other than the xenon lamp. Thus, the light source can be any one that emits a broadband light. The optical filter 2A is a filter that transmits only light of a specific band of the broadband light emitted from the light source. For example, the optical filter 2A transmits light of a band whose central wavelength is about 760 nm and whose wavelength width is about 100 nm, of the broadband light emitted from the light source.

Further, the CCDs 21 and 22 of the optical image measuring apparatus change the exposure time (the light storage time) in response to control signals from the computer 30. A function of controlling the exposure time corresponds to a function which is normally called an "electronic shutter" or the like. The computer 30 (particularly the controller 31: see FIG. 5) operates as an example of the "exposure-time changer" in the present invention.

The computer 30 sets the exposure time for each of the polarization components L1 and L2 detected by the CCDs 21 and 22 to a time shorter than a frame rate thereof, preferably, a time sufficiently shorter than the frame rate. With the electronic shutter function, it is possible to control the exposure time more minutely than in the case of using a mechanical shutter.

First, in order to measure a background light component, the computer 30 makes the light source emit a measurement light in a state where the optical-path-length changing optical element 9 is retracted from the optical path of the reference light R. The CCD 21 or 22 receives this measurement light, and inputs a detection signal into the computer 30.

Next, the computer 30 makes the optical-path-length changing optical element 9 inserted into the optical path of the reference light R, and also changes the exposure time of the CCDs 21 and 22 to the short time as described above. The measurement light is emitted from the light source in this state, and the polarization components L1 and L2 of the interference light L are detected by the CCDs 21 and 22. The CCDs 21 and 22 each input a detection signal to the computer 30.

The computer 30 (particularly the signal processor 20: refer to FIG. 5) executes a process similar to that in the above embodiment to form an image, based on the three detection signals inputted from the CCDs 21 and 22.

According to the optical image measuring apparatus thus configured, it is possible to change the exposure time of the CCDs 21 and 22. Therefore, by setting the exposure time to a sufficiently short time, it becomes possible to form a highly accurate image without an influence of movement of the measurement object. Moreover, the optical image measuring apparatus forms an image by using the polarization characteristics of the interference light instead of using a conventional mechanical light cutoff device (shutter), so that there is a merit that it is unnecessary to perform complicated synchronization control.

The exposure time of the CCD 21 or 22 in measurement of the background light component may also be set to the short time as described above.

Further, a measurement light emitted from the light source of the optical image measuring apparatus may be pulse light. This pulse light has a light emission time shorter than the frame rate of the CCDs 21 and 22. Moreover, the computer 30 sets the exposure time for the polarization components L1 and L2 detected by the CCDs 21 and 22 to a time shorter than the light emission time of the pulse light (specifically, a time substantially equal to or shorter than the light emission time). Even with such a configuration, it is possible to produce the same actions and advantageous effects as those in the above-mentioned optical image measuring apparatus.

Hereinafter, various modifications applicable to the optical image measuring apparatuses according to the aforementioned embodiments and the aforementioned modifications will be described. First, in the configurations of the aforementioned embodiments etc., the background light component is measured when the optical-path-length changing optical element 9 is inserted into the optical path of the reference light R, and the interference light L is measured when the optical-path-length changing optical element 9 is retracted from the optical path of the reference light R. However, it is also possible to configure reversely. That is, by setting the position of the reference mirror 8 when the optical-path-length changing optical element 9 is inserted so as to coincide with the depth z=z1 to zN of the measurement object O, it is possible to configure to measure the background light component when the optical-path-length changing optical element 9 is retracted from the optical path, and measure the interference light L when the optical-path-length changing optical element 9 is inserted into the optical path. The calculation process for image formation in this case is similar to the above.

Further, in the aforementioned embodiments etc., the background light component is measured before the measurement of the interference light L. However, it is possible to arbitrarily set timing for measuring the background light component. For example, the background light component may be measured after the measurement of the interference light L. Moreover, in the case of measuring the interference light L corresponding to a plurality of depths while performing z-scan, it is possible to measure the background light component at any timing during the z-scan.

Further, by providing a wavelength plate (½-wavelength plate) on the optical path of the signal light S, namely, between the half mirror 6 and the measurement object O in the configuration shown in FIG. 4, it becomes possible to correct the tilt of the polarization direction of the signal light S caused by a change in phase when the signal light S propagates through the measurement object O.

Further, in the above-mentioned embodiments etc., the polarization characteristic of the reference light R is converted into circular polarization. However, it is also possible to dispose the wavelength plate 7 on the optical path of the signal light S, thereby configuring to convert the polarization characteristic of the signal light S into circular polarization.

The detector applicable to the optical image measuring apparatus according to the present invention is not limited to a CCD. It is possible to use any optical sensor, such as a CMOS sensor, that detects interference light with 2-dimensionally arranged pixels and performs photoelectric conversion to output a detection signal.

In the above-mentioned embodiments etc., the optical image measuring apparatus including the Michelson type interferometer is described. However, it is also possible to employ an interferometer such as a Mach-Zehnder type interferometer (see, for example, Japanese Patent 3245135 by the inventors of the present invention).

Further, by disposing and using an optical fiber (bundle) as a light guide member in part of the interferometer, it is possible to increase the degree of freedom of an apparatus design, make the apparatus compact in size, or increase the degree of freedom of location of the measurement object (see, for example, Japanese Patent 3245135 described above).

When the optical image measuring apparatus according to the present invention is applied to, for example, the ophthalmologic field, it is possible to not only measure a blood flow state of a fundus oculi but also acquire a 2-dimensional tomographic image etc. of retina or cornea. Consequently, it becomes possible to measure, for example, the number of endothelial cells of the cornea. It is needless to say that the optical image measuring apparatus can be applied to various other fields.

Third Embodiment

[Configuration of Apparatus]

A third embodiment of the optical image measuring apparatus according to the present invention will be described. The configuration of the optical image measuring apparatus of this embodiment is shown in FIG. 6.

Figure 6:
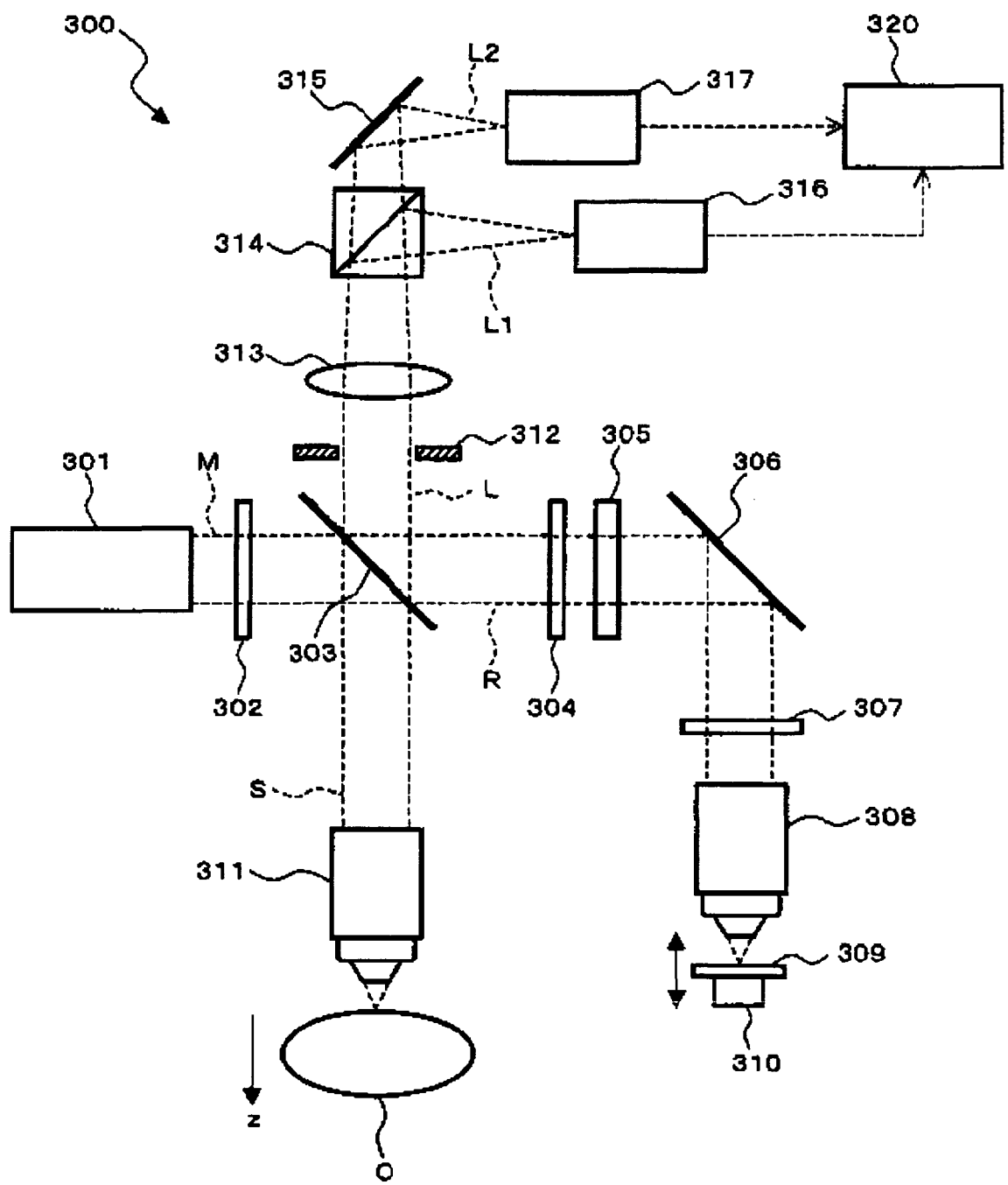
FIG. 6 is a schematic diagram showing an example of a configuration in an embodiment of the optical image measuring apparatus according to the present invention.

The measurement object O in FIG. 6 is placed appropriately for measurement. For example, the measurement object O is placed in the liquid immersion state in order to reduce a change in refractive index at the boundary. Further, in a case where the measurement object O is a living body etc., it is possible to apply jerry, liquid or the like for reducing a change in refractive index at the boundary to the measurement object O.

An optical image measuring apparatus 300 shown in FIG. 6 comprises a halogen lamp 301 as a light source. The halogen lamp 301 corresponds to an example of the "light-emitting part" of the present invention, which emits a non-polarized broadband light M. The halogen lamp 301 includes a normal halogen lamp, and further includes an optical fiber bundle that guides the emitted light, a Kohler illumination optical system for uniformly illuminating an illumination field of the emitted light, etc. (not illustrated in the drawing). The non-polarized broadband light M emitted from the halogen lamp 301 has a specific beam diameter.

As the light-emitting part in this embodiment, it is possible to apply, other than the halogen lamp, any light source that emits a non-polarized broadband light. For example, it is possible to apply any thermal light source (a light source based on black-body radiation) such as a xenon lamp. Further, the light-emitting part in this embodiment may be a laser light source that emits a random-polarized broadband light. "Non-polarized" means a polarization state including a linearly polarized light, a circularly polarized light and an elliptically polarized light. "Random-polarized" means a polarization state including two linear-polarization components orthogonal to each other, in which the power of each of the linear-polarization components changes temporally randomly (refer to Japanese Unexamined Patent Application Publication JP-A 7-92656, for example). Hereinafter, only a case of non-polarization will be described in detail. However, also in the case of random-polarization, it is possible to obtain similar actions and advantageous effects with a similar configuration.

Now, the broadband light M emitted by the halogen lamp 301 contains lights of various bands. A filter 302 is a filter that transmits only a specific band of the non-polarized broadband light M. The specific band to transmit is determined based on resolution, measurement depth, etc. For example, it can be set to a band whose central wavelength is about 760 nm and wavelength width is about 100 nm. In this case, in a depth direction (z-direction shown in FIG. 6) of the measurement object O and a direction (lateral direction) orthogonal thereto, it is possible to acquire images with resolution of 2 μm, respectively. The light transmitted through the filter 302 will also be referred to as the broadband light M.

The non-polarized broadband light M transmitted through the filter 302 is split into two by a beam splitter 303 such as a half mirror. A light reflected by the beam splitter 303 forms the signal light S, and a light transmitted through the beam splitter 303 forms the reference light R.

The signal light S is focused onto the measurement object O by an objective lens 311, while maintaining the non-polarized state. Light reflected or scattered by the surface or inside of the measurement object O passes through the objective lens 311 and returns to the beam splitter 303.

The non-polarized reference light R generated by the beam splitter 303 passes through a wavelength plate (π/4 plate) and a polarizing plate 305, and is reflected by a reflection mirror 306. Further, the reference light R passes through a glass plate 307, and is focused on the reflection face of a reference mirror 309 by an objective lens 308. The reference light R reflected by the reference mirror 309 reversely travels on the same optical path and returns to the beam splitter 303.

The reference mirror 309 is moved by a reference-mirror moving mechanism 310 in a traveling direction of the reference light R, that is, in a direction (a direction of double-headed arrow in FIG. 6) orthogonal to the reflection face of the reference mirror 309. The reference-mirror moving mechanism 310 includes a piezo element or the like. The reference-mirror moving mechanism 310 is capable of switching the optical path length of the reference light R between a "first optical path length" and a "second optical path length" by moving the reference mirror 309.

The reference light R having been non-polarized initially is converted into a circular-polarized light while traveling between the wavelength plate 304 and the polarizing plate 305 two times. The glass plate 307 is a dispersion-correction optical element that minimizes the influence of dispersion occurring in the optical paths of the signal light S and the reference light R (both arms of the interferometer).

The signal light S returned from the measurement object O and the reference light R returned from the reference mirror 309 are superimposed by the beam splitter 303, whereby the interference light L is generated. The interference light L contains the S-polarization component and the P-polarization component as in the first and second embodiments.

The interference light L generated by the beam splitter 303 travels through an aperture diaphragm 312, and becomes a focused light through an imaging lens (group) 313. The S-polarization component L1 of the interference light L having become a focused light is reflected by a polarized beam splitter 314, and detected by a CCD (image sensor) 316. On the other hand, the P-polarization component L2 of the interference light L is transmitted through the polarized beam splitter 314, reflected by a reflection mirror 315, and detected by a CCD (image sensor) 317.

The CCDs 316 and 317 having detected the S-polarization component L1 and the P-polarization component L2 send detection signals (first and second detection signals) to the computer 320, respectively.

Because the reference light R and the signal light S for generating the interference light L are a circular-polarized light and a non-polarized light, respectively, the S-polarization component L1 and the P-polarization component L2 have a phase difference of 90 degrees (π/2). Therefore, a detection signal $C_A$ outputted from the CCD 316 and a detection signal $C_B$ outputted from the CCD 317 have a phase difference of 90 degrees, and can be expressed by the following formula.

Formula (2)

$$C_A(x, y) = I_s(x, y) + I_r(x, y) + \sqrt{I_s(x, y)I_r(x, y)} \cos(\Delta\phi(x, y)) \quad (2)$$

$$C_B(x, y) = I_s(x, y) + I_r(x, y) + \sqrt{I_s(x, y)I_r(x, y)} \sin(\Delta\phi(x, y)) \quad (3)$$

In the above formula, $I_s(x,y)$ presents the intensity of the signal light S, and $I_r(x,y)$ presents the intensity of the reference light R. $\phi(x,y)$ presents an initial phase difference. The respective detection signals $C_A$ and $C_B$ contain a background light component (noninterference component, DC component) $I_s(x,y)+I_r(x,y)$. Furthermore, the detection signal $C_A$ contains an interference component composed of a cos component, and the detection signal $C_B$ contains an interference component composed of a sin component.

As apparent from the equations (2) and (3), the respective detection signals $C_A$ and $C_B$ contain only space (the x-direction and y-direction that are orthogonal to the z-direction) as variables, and do not contain time as a variable. That is, an interference signal in this embodiment contains only a spatial change, and is different from the interference signals (AC signals) in the first and second embodiments.

[Configuration of Control System]

Figure 7:
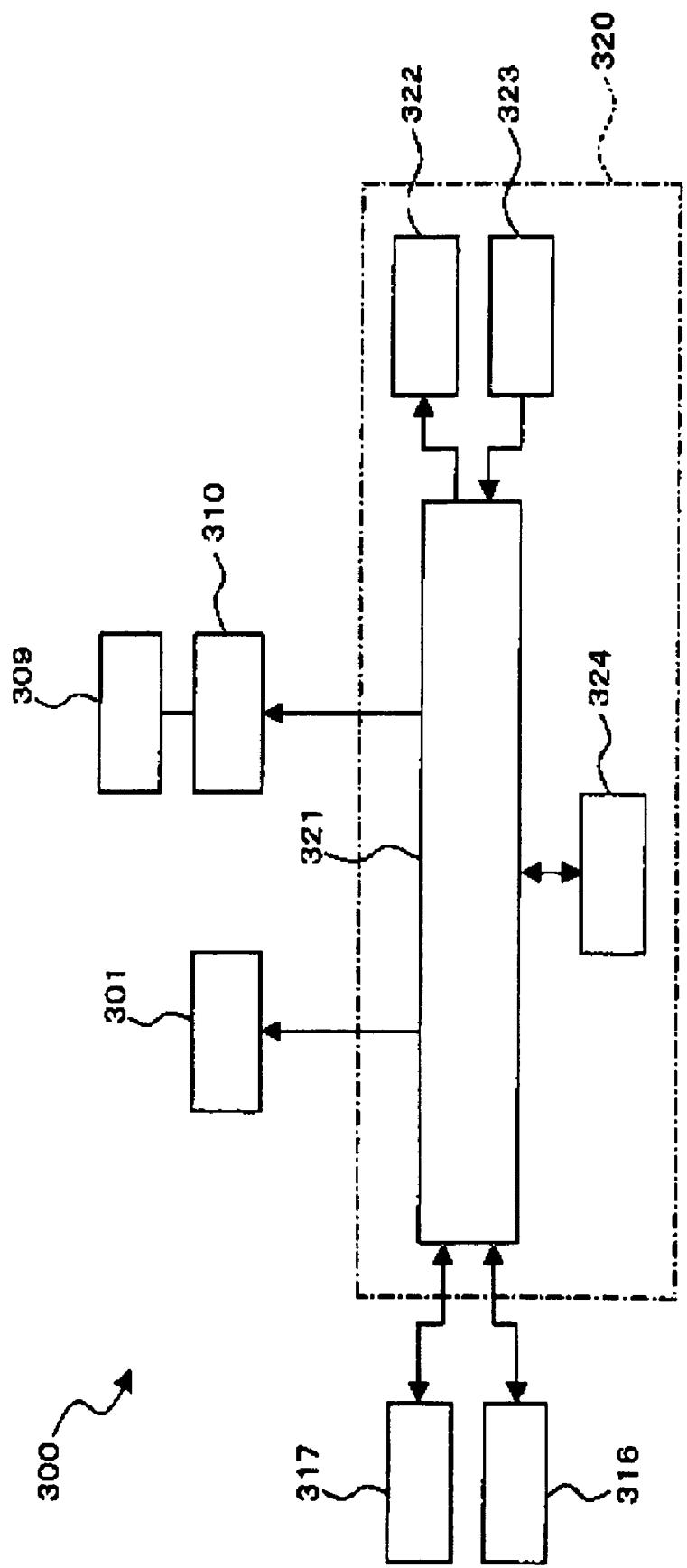
FIG. 7 is a schematic block diagram showing an example of a configuration of a control system in the embodiment of the optical image measuring apparatus according to the present invention.

A configuration of a control system of the optical image measuring apparatus 300 in this embodiment will be described. FIG. 7 shows an example of the configuration of the control system of the optical image measuring apparatus 300.

A computer 320 is provided with a controller 321, a display 322, an operation part 323, and a signal processor 324, as in the first and second embodiments. The controller 321 executes control to turn on/off the halogen lamp 301, control of the reference-mirror moving mechanism 310, control of the exposure time of the CCDs 316 and 317, and so on. The signal processor 324 forms an image of the measurement object O based on the detection signals $C_A$ and $C_B$ outputted from the CCDs 316 and 317.

The optical image measuring apparatus 300 in this embodiment may comprise the optical detector (2C) and the image regulation processor (205), as in the first and second embodiments.

[Operation Mode]

An operation mode of the optical image measuring apparatus 300 in this embodiment having the above configuration will be described.

First, the controller 321 turns on the halogen lamp 301. In this operation mode, a continuous light of the broadband light M is outputted while the halogen lamp 301 is kept turned on.

Next, the controller 321 controls the reference-mirror moving mechanism 310 to set the optical path length of the reference light R to a "first optical path length." Then, the controller 321 controls the exposure time of each of the CCDs 316 and 317 so that the detection signals $C_A$ and $C_B$ are outputted.

Next, the controller 321 controls the reference-mirror moving mechanism 310 to switch the optical path length of the reference light R to a "second optical path length," and also controls the exposure time of each of the CCDs 316 and 317 so that new detection signals $C_A'$ and $C_B'$ are outputted.

Here, the first optical path length and the second optical path length of the reference light R are previously set to a distance interval such that the detection signals $C_A$ and $C_A'$ have a phase difference of 180 degrees ($\pi$) and the detection signal $C_B$ and $C_B'$ have a phase difference of 180 degrees ($\pi$). The detection signals $C_A$ and $C_B$ have a phase difference of 90 degrees, and therefore, four detections signals $C_A, C_B, C_A'$ and $C_B'$ by phase difference of 90 degrees are obtained.

The signal processor 324 calculates the background light component $I_s(x,y)+I_r(x,y)$ by adding the detection signals $C_A$ and $C_A'$ (phase difference: 180 degrees) and dividing the sum by 2. This calculation process may be executed by using the detection signals $C_B$ and $C_B'$ (phase difference: 180 degrees).

Furthermore, the signal processor 324 calculates the interference components (cos component, sin component) by subtracting the calculated background light component $I_s(x,y)+I_r(x,y)$ from the respective detection signals $C_A$ and $C_B$. Then, the signal processor 324 forms an image in cross section along the x-y direction by calculating the square sum of the interference components of the respective detection signals $C_A$ and $C_B$. The controller 321 causes the display 322 to display the formed image in response to, for example, an operation through the operation part 323. This image formation process may be executed by using the detection signals $C_A'$ and $C_B'$ (phase difference: 180 degrees).

The optical image measuring apparatus 300 iterates while changing the optical path length of the signal light S or reference light R, thereby sequentially forming x-y cross-sectional images at various depth positions (z=z1 to zN) of the measurement object O.

In the case of changing the optical path length of the signal light S, it is possible to dispose the optical system shown in FIG. 6 onto a stage and configure so as to move this stage in the z direction by a driving mechanism. It is also possible to configure to change the optical path length of the signal light S by positioning the measurement object O on the similar stage. On the other hand, in the case of changing the optical path length of the reference light R, it is possible to configure to move the reference mirror 309 by the reference-mirror moving mechanism 310, for example.

Further, in the aforementioned process of sequentially forming the cross-sectional images, the controller 321 controls the CCDs 316 and 317 to output the detection signals at a specific frame rate and at the same timing, and also synchronizes the frame rate, the exposure timing of each of the CCDs 316 and 317, the movement timing of the reference mirror 309, and the change timing of the optical path length of the signal light S (reference light R).

At this moment, the exposure time of each of the CCDs 316 and 317 is set shorter than the frame rate. For example, it is possible to set the frame rate of each of the CCDs 316 and 317 to 30 f/s, and set the exposure time thereof to 30 to 50 µs.

Further, it is possible to acquire an image with resolution of a few µm by using the broadband light M whose central wavelength is about 760 nm and wavelength width is about 100 nm. For example, assuming the wavelength of the broadband light M is Gaussian, the theoretical figure of the resolution is approximately 1.8 µm when the refractive index of the measurement object O is n=1.33.

[Actions and Advantageous Effects]

According to the optical image measuring apparatus 300 of this embodiment acting as described above, the following actions and advantageous effects are produced.

The optical image measuring apparatus 300 splits the (non-polarized) broadband light M outputted from the halogen lamp 301 into the signal light S and the reference light R, and converts the polarization characteristic of the reference light R (to circular polarization). Then, the optical image measuring apparatus 300 generates the interference light L by superimposing the reference light R having the converted polarization characteristic with the signal light S, extracts two polarization components (S-polarization component and P-polarization component) of the interference light L, and detects the components by the CCDs 316 and 317. Then, the optical image measuring apparatus 300 forms an image of the measurement object O based on the detection signals $C_A$ and $C_B$ ($C_A'$ and $C_B'$) outputted from the CCDs 316 and 317.

Thus, because the optical image measuring apparatus 300 is capable of simultaneously acquiring two polarization components of the interference light L, it is possible to shorten the measurement time. To be specific, because it is configured to acquire the four detection signals $C_A, C_B, C_A'$ and $C_B'$ having different phases in two measurements to form an image, it is possible to shorten the measurement time.

Further, because the optical image measuring apparatus 300 can easily and quickly switch acquisition of the detection signals $C_A$ and $C_B$ and acquisition of the detection signals $C_A'$ and $C_B'$ only by switching the optical path length of the reference light R, it is possible to shorten the measurement time.

Further, because the optical image measuring apparatus 300 can simultaneously detect the two polarization components L1 and L2 of the interference light L, and there is no error in detection time between the two polarization components L1 and L2, it is possible to form a highly accurate image without an influence of movement of the measurement object O.

Further, there is a merit that use of the non-polarized broadband light M facilitates the configuration of the optical system. That is, in a case where a broadband light in a polarization condition such as linear polarization, the polarization condition of the broadband light may be influenced when the broadband light passes through a beam splitter or a lens, and hence, there is a problem that the configuration of the optical system for maintaining the polarization condition is difficult.

However, it is possible to simplify the configuration of the optical system by using the non-polarized broadband light M as in this embodiment.

Further, it is possible to easily obtain a non-polarized broadband light by using a thermal light source as the light-emitting part or using an optical fiber bundle. Also in the case of using a laser light source that emits a random-polarized broadband light, it is possible to easily obtain the random-polarized broadband light.

Further, by disposing the glass plate 307 serving as the dispersion-correction optical element that minimizes the influence of dispersion occurring on the optical paths of the signal light S and reference light R (both arms of the interferometer), it is possible to eliminate a difference in dispersion between the signal light S and the reference light R, and it is possible to efficiently acquire the interference light L on which information included in the signal light S is favorably reflected.

Further, by performing measurement in a state where the exposure times of the CCDs 316 and 317 are set short, it is possible, even if the measurement object O has moved during the measurement, to form a highly accurate image without an influence of the movement.

Further, because it is possible to perform measurement in a state where the exposure times of the CCDs 316 and 317 are set short while outputting a continuous light of the broadband light M, it is possible to form an image of the measurement object O without executing complicated control of the light cut-off device or the light source as executed conventionally.

Further, because a band suitable for measurement is extracted by the filter 302 from the broadband light M emitted by the halogen lamp 301 and the band is used, it is possible to acquire a favorable image.

[Modification]

A modification of the optical image measuring apparatus 300 according to this embodiment will be described.

Figure 8:
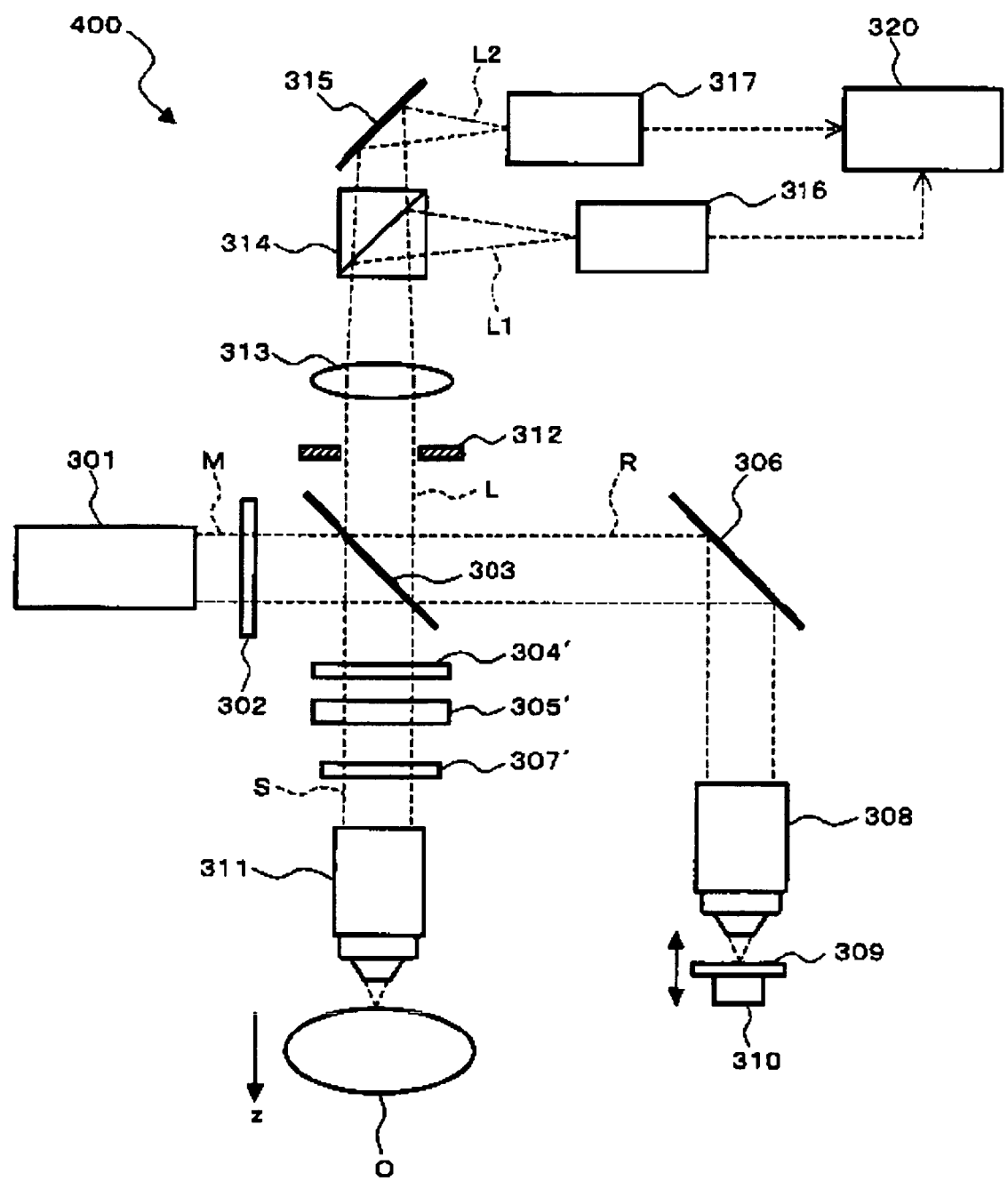
FIG. 8 is a schematic diagram showing an example of a configuration in a modification of the embodiment of the optical image measuring apparatus according to the present invention.
Figure 9:
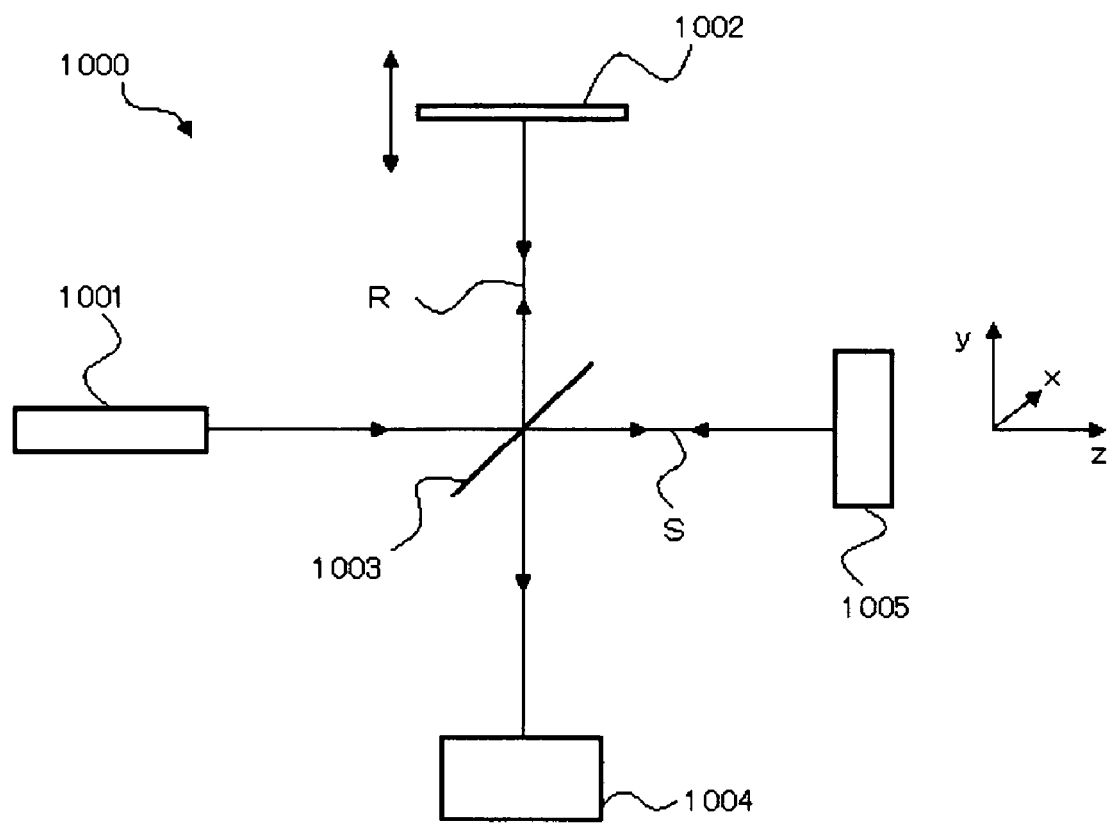
FIG. 9 is a schematic diagram showing a configuration of a conventional optical image measuring apparatus.
Figure 10:
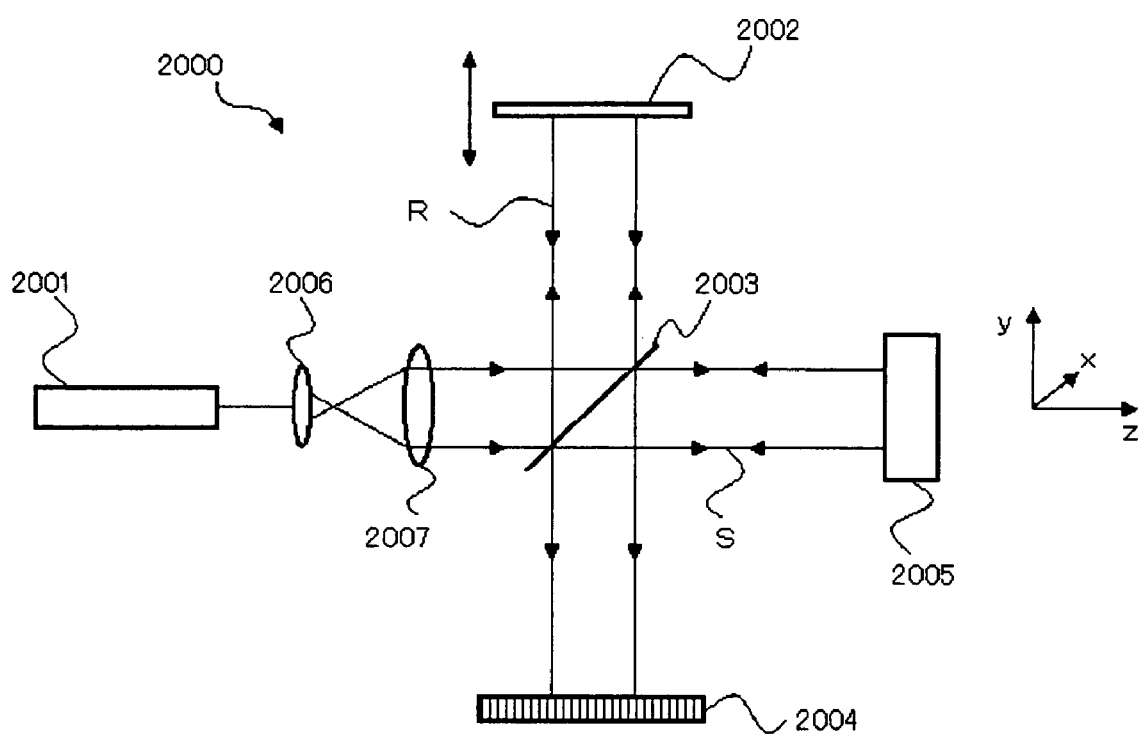
FIG. 10 is a schematic diagram showing a configuration of a conventional optical image measuring apparatus.

The aforementioned optical image measuring apparatus 300 is configured to convert the polarization characteristic of the reference light R. On the other hand, an optical image measuring apparatus 400 shown in FIG. 8 converts the polarization characteristic of the signal light S. For this, the optical image measuring apparatus 400 comprises the reflection mirror 306 and the objective lens 308 that are provided on the optical path of the reference light R, and comprises a wavelength plate (π/4 plate) 304', a polarizing plate 305' and a glass plate 307' that are provided on the optical path of the signal light S.

The signal light S is converted into a circular-polarized light by the wavelength plate 304' and the polarizing plate 305', and subjected to dispersion correction by the glass plate 307'. On the other hand, the reference light R is not subjected to polarization characteristic conversion, and is superimposed with the signal light S while maintaining a non-polarization (random-polarization) condition.

According to the optical image measuring apparatus 400, as in the aforementioned optical image measuring apparatus 300, it is possible to shorten the measurement time, it is possible to form a highly accurate image without an influence of movement of the measurement object O, and it is possible to form an image of the measurement object O without executing complicated control of the light-cutoff device or the light source.

In the aforementioned optical image measuring apparatus 300, a non-polarized or random-polarized broadband light is emitted by a thermal light source such as a halogen lamp and a xenon lamp or a laser light source. However, it is possible to appropriately use any type of light-emitting part capable of emitting a non-polarized or random-polarized broadband light.

The aforementioned optical image measuring apparatus 300 uses the wavelength plate 304 and the polarizing plate 305 to convert the polarization characteristic, but may use any type of converter capable of converting the polarization characteristic. Moreover, although the reference light R is converted into a circular-polarized light in the aforementioned embodiment, it is possible, depending on the configuration of the optical image measuring apparatus, to configure to convert the reference light R or the signal light S to have any polarization characteristic (linear polarization, elliptic polarization).

Although the aforementioned optical image measuring apparatus 300 corrects dispersion occurring at both the arms of the interferometer by using the glass plate 307, it is also possible to apply a dispersion-correction optical element such as an optical element of any type that can correct dispersion.

Although the aforementioned optical image measurement apparatus 300 uses the CCDs 316 and 317 as the first and second detectors, it is possible to apply any type of photodetector such as a CMOS.

The aforementioned optical image measuring apparatus 300 handles movement of the measurement object O, etc., by using a continuous light of a broadband light and setting the exposure times of the CCDs 316 and 317 short. However, this configuration is not a limitation.

For example, it is possible to dispose an optical chopper on the optical path of the broadband light (continuous light) emitted by the light-emitting part, periodically blocks the broadband light by the optical chopper to generate a pulsed broadband light, and detect each pulse by the CCDs 316 and 317. With this configuration, it is possible to favorably acquire an image even if the measurement object O has moved, as in the optical image measuring apparatus 300.

The period of blocking the broadband light by the optical chopper is about 1 ms, and is longer than the exposure time (30 to 50 μs). Therefore, it is desirable to control the exposure time in a case where movement of the measurement object O is rapid.

Further, it is also possible to configure to emit a broadband light composed of flash lights by using a light source such as a xenon lamp, and detect each of the flash lights by the CCDs 316 and 317.

Further, as mentioned in the description of the optical image measuring apparatus 300, it is possible to configure to obliquely dispose a beam splitter on the optical path of a broadband light emitted by the light-emitting part to derive part of the broadband light, detect the part of the broadband light by a photodetector such as a photodiode to output a detection signal to the computer 320, and correct the brightness value or lightness value of an image by an image regulation processor (functions in the same manner as the image regulation processor 205 shown in FIGS. 2 and 5) of the computer 320.

Further, although the aforementioned optical image measuring apparatus 300 acquires the two detection signals $C_A$ and $C_B$ ($C_A'$ and $C_B'$) having a phase difference of 90 degrees in one measurement, it may acquire the two detection signals having a phase difference of 180 degrees by using a π/2 plate as the wavelength plate 304. In this case, the first optical path length and second optical path length of the reference light R are preset to a distance interval such that a detection signal obtained in a first detection process and a detection signal obtained in a second detection process have a phase difference of 90 degrees. Consequently, it is possible to acquire four detection signals by phase difference of 90 degrees.

In the above-mentioned embodiment or the like, the optical image measuring apparatus including the Michelson type interferometer is described. However, it is also possible to employ another interferometer such as a Mach-Zehnder type interferometer (see, for example, Japanese Patent JP 3245135 made by the inventors of the present invention).

Further, by providing an optical fiber (bundle) used as a light guide member in part of the interferometer, it is possible to increase the degree of freedom of an apparatus design, make the apparatus compact in size, or increase the degree of freedom of location of the measurement object (see, for example, JP 3245135 described above).

When the optical image measuring apparatus according to the present invention is applied to, for example, an ophthalmologic field, it is possible to acquire a 2-dimensional cross-sectional image of retina and cornea in addition to a blood flow state obtained by blood flow measurement on an eye fundus. Consequently, it is possible to measure, for example, the number of endothelial cells of the cornea. It is needless to say that various other applications are also possible.

What is claimed is:

1. An optical image measuring apparatus, comprising:
a light-emitting part configured to emit a broadband light;
a splitter configured to split the emitted broadband light into a signal light heading to a measurement object and a reference light heading to a reference object;
a converter configured to convert a polarization characteristic of the signal light or the reference light;
a superimposing part configured to superimpose one of the signal light returned from the measurement object and the reference light returned from the reference object onto the other to generate interference light, the one of the signal light and the reference light having the converted polarization characteristic;
an extracting part configured to extract two different polarization components of the generated interference light;
a first detector configured to detect one of the two polarization components having been extracted and output a first detection signal, and a second detector configured to detect the other and output a second detection signal;
a third detector configured to detect light originating from the broadband light emitted by the light-emitting part and output a third detection signal; and
an image formation processor configured to form an image of the measurement object, based on the first, second and third detection signals, wherein, the image formation processor includes:
a background-light calculator configured to calculate a background light component of the interference light, based on the third detection signal; and
an interference-component-intensity calculator or a phase-distribution calculator, wherein
the interference-component-intensity calculator is configured to calculate a signal intensity of an interference component of each of the two polarization components, based on the calculated background light component and the first and second detection signals; and
the phase-distribution calculator is configured to calculate a spatial phase distribution of the interference light, based on the calculated background light component and the first and second detection signals, wherein
the image formation processor is configured to form the image of the measurement object, based on the calculated signal intensity of the interference component of each of the two polarization components, or configured to an image showing the calculated spatial phase distribution.

2. An optical image measuring apparatus according to claim 1, further comprising:
an optical-path-length changer configured to change a difference in optical path length between the signal light and the reference light, wherein:
the light-emitting part emits another flash light when the optical path length is changed after a flash light as the broadband light is emitted; and
the image formation processor forms another image of the measurement object, based on the first, second and third detection signals originating from the another flash light.

3. An optical image measuring apparatus according to claim 2, wherein:
the optical-path-length changer continuously changes the optical path length of the reference light;
the light-emitting part intermittently emits the flash light; and
the image formation processor forms an image of the measurement object, based on the first, second and third detection signals originating from each of the flash lights intermittently emitted.

4. An optical image measuring apparatus according to claim 2, wherein:
the optical-path-length changer intermittently changes the difference in optical path length;
a controller is further comprised, which is configured to synchronize a timing of intermittent emission of the flash light by the light-emitting part with a timing of intermittent change of the difference in optical path length by the optical-path-length changer; and
the image formation processor forms an image of the measurement object, based on the first, second and third detection signals originating from each of the flash lights emitted at the synchronized emission timing.

5. An optical image measuring apparatus according to claim 1, further comprising:
an exposure-time changer configured to change an exposure time for the polarization component by each of the first and second detectors, wherein:
the image formation processor forms the image of the measurement object, based on the first and second detection signals originating from the polarization components detected in the changed exposure time and based on the third detection signal.

6. An optical image measuring apparatus according to claim 5, wherein:
the first and second detectors output the first and second detection signals, respectively, at a specific frame rate; and
the exposure-time changer changes the exposure time by each of the first and second detectors to a time shorter than the specific frame rate.

7. An optical image measuring apparatus according to claim 5, wherein:
the first and second detectors output the first and second detection signals, respectively, at a specific frame rate;
the light-emitting part emits the broadband light whose emission time is shorter than the specific frame rate; and
the exposure-time changer changes the exposure time by each of the first and second detectors to a time shorter than the emission time of the broadband light.

8. An optical image measuring apparatus according to claim 1, wherein:
- the first, second and third detectors output the first, second and third detection signals, respectively, at a specific frame rate;
- the light-emitting part intermittently emits a flash light as the broadband light at a timing synchronized with the specific frame rate; and
- for each of the flash lights emitted intermittently, the image forming processor forms the image of the measurement object, based on the first, second and third detection signals originating from the flash light.

9. An optical image measuring apparatus comprising:
- a light-emitting part configured to emit a broadband light;
- a splitter configured to split the emitted broadband light into a signal light heading to a measurement object and a reference light heading to a reference object;
- a converter configured to convert a polarization characteristic of the signal light or the reference light;
- a superimposing part configured to superimpose one of the signal light returned from the measurement object and the reference light returned from the reference object onto the other to generate interference light, the one of the signal light and the reference light having the converted polarization characteristic;
- an extracting part configured to extract two different polarization components of the generated interference light;
- a first detector configured to detect one of the two polarization components having been extracted and output a first detection signal, and a second detector configured to detect the other and output a second detection signal;
- an image formation processor configured to form an image of the measurement object, based on the first and second detection signals outputted by the first and second detectors; and
- an optical-path-length changing member configured to be insertable into and retractable from an optical path of the signal light or the reference light, thereby changing a length of the optical path, wherein:
- the image formation processor forms the image of the measurement object, based on the first and second detection signals outputted from the first and second detectors when the optical-path-length changing member is retracted from the optical path, and a fourth detection signal outputted by the first or second detector when the optical-path-length changing member is inserted into the optical path.

10. An optical image measuring apparatus according to claim 9, wherein:
- the reference object is a reference mirror having a reflection face positioned orthogonally to the optical path of the reference light;
- a reference-mirror moving mechanism is further comprised, which is configured to move the reference mirror in a direction of the optical path of the reference light, thereby changing the optical path length of the reference light;
- the light-emitting part emits another flash light when the optical path length of the reference light is changed after a flash light as the broadband light is emitted, in a state where the optical-path-length changing member is retracted from the optical path; and
- the image formation processor forms another image of the measurement object, based on the first and second detection signals originating from the another flash light and based on the fourth detection signal.

11. An optical image measuring apparatus according to claim 10, wherein:
- the reference-mirror moving mechanism continuously moves the reference mirror in the optical path direction;
- the light-emitting part intermittently emits the flash light; and
- for each of the flash lights emitted intermittently, the image formation processor forms an image of the measurement object, based on the first and second detection signals originating from the flash light and based on the fourth detection signal.

12. An optical image measuring apparatus according to claim 10, wherein:
- the reference-mirror moving mechanism intermittently moves the reference mirror in the optical path direction;
- a controller is further comprised, which is configured to synchronize a timing of intermittent emission of the flash light by the light-emitting part with a timing of intermittent movement of the reference mirror by the reference-mirror moving mechanism; and
- the image formation processor forms an image of the measurement object, based on the first and second detection signals originating from each of the flash lights emitted at the synchronized emission timing and based on the fourth detection signal.

13. An optical image measuring apparatus according to claim 9, further comprising:
- an exposure-time changer configured to change an exposure time for the polarization component by each of the first and second detectors, wherein:
- the image formation processor forms the image of the measurement object, based on the first and second detection signals originating from the polarization components detected in the changed exposure time and based on the fourth detection signal.

14. An optical image measuring apparatus according to claim 13, wherein:
- the first and second detectors output the first and second detection signals, respectively, at a specific frame rate; and
- the exposure-time changer changes the exposure time by each of the first and second detectors to a time shorter than the specific frame rate.

15. An optical image measuring apparatus according to claim 13, wherein:
- the first and second detectors output the first and second detection signals, respectively, at a specific frame rate;
- the light-emitting part emits the broadband light whose emission time is shorter than the specific frame rate; and
- the exposure-time changer changes the exposure time by each of the first and second detectors to a time shorter than the emission time of the broadband light.

16. An optical image measuring apparatus according to claim 9, wherein:
- the image formation processor includes:
  - a background-light calculator configured to calculate a background light component of the interference light, based on the fourth detection signal; and
  - an interference-component-intensity calculator configured to calculate a signal intensity of an interference component of each of the two polarization components, based on the calculated background light component and the first and second detection signals; and
- the image formation processor forms the image of the measurement object, based on the calculated signal intensity of the interference component of each of the two polarization components.

17. An optical image measuring apparatus according to claim 9, wherein:
the image formation processor includes:
a background-light calculator configured to calculate a background light component of the interference light, based on the fourth detection signal; and
a phase-distribution calculator configured to calculate a spatial phase distribution of the interference light, based on the calculated background light component and the first and second detection signals; and
the image formation processor forms an image showing the calculated spatial phase distribution.

18. An optical image measuring apparatus according to claim 9, wherein:
the first and second detectors output the first and second detection signals, respectively, at a specific frame rate;
the light-emitting part intermittently emits a flash light as the broadband light at a timing synchronized with the specific frame rate, when the optical-path-length changing member is retracted from the optical path; and
for each of the flash lights emitted intermittently, the image forming processor forms the image of the measurement object, based on the first and second detection signals originating from the flash light and based on the fourth detection signal.

19. An optical image measuring apparatus comprising:
a light-emitting part configured to emit a broadband light;
a splitter configured to split the emitted broadband light into a signal light heading to a measurement object and a reference light heading to a reference object;
a converter configured to convert a polarization characteristic of the signal light or the reference light;
a superimposing part configured to superimpose one of the signal light returned from the measurement object and the reference light returned from the reference object onto the other to generate interference light, the one of the signal light and the reference light having the converted polarization characteristic;
an extracting part configured to extract two different polarization components of the generated interference light;
a first detector configured to detect one of the two polarization components having been extracted and output a first detection signal, and a second detector configured to detect the other and output a second detection signal;
an image formation processor configured to form an image of the measurement object, based on the first and second detection signals outputted by the first and second detectors; and
an optical-path-length changing member configured to be insertable into and retractable from an optical path of the signal light or the reference light, thereby changing a length of the optical path, wherein:
the image formation processor forms the image of the measurement object, based on the first and second detection signals outputted from the first and second detectors when the optical-path-length changing member is inserted into the optical path, and a fourth detection signal outputted by the first or second detector when the optical-path-length changing member is retracted from the optical path.

20. An optical image measuring apparatus according to claim 19, wherein:
the reference object is a reference mirror having a reflection face positioned orthogonally to the optical path of the reference light;
a reference-mirror moving mechanism is further comprises, which is configured to move the reference mirror in a direction of the optical path of the reference light, thereby changing the optical path length of the reference light;
the light-emitting part emits another flash light when the optical path length of the reference light is changed after a flash light as the broadband light is emitted, in a state where the optical-path-length changing member is inserted into the optical path; and
the image formation processor forms another image of the measurement object, based on the first and second detection signals originating from the another flash light and based on the fourth detection signal.

21. An optical image measuring apparatus according to claim 20, wherein:
the reference-mirror moving mechanism continuously moves the reference mirror in the optical path direction;
the light-emitting part intermittently emits the flash light; and
for each of the flash lights emitted intermittently, the image formation processor forms an image of the measurement object, based on the first and second detection signals originating from the flash light and based on the fourth detection signal.

22. An optical image measuring apparatus according to claim 20, wherein:
the reference-mirror moving mechanism intermittently moves the reference mirror in the optical path direction;
a controller is further comprised, which is configured to synchronize a timing of intermittent emission of the flash light by the light-emitting part with a timing of intermittent movement of the reference mirror by the reference-mirror moving mechanism; and
the image formation processor forms an image of the measurement object, based on the first and second detection signals originating from each of the flash lights emitted at the synchronized emission timing and based on the fourth detection signal.

23. An optical image measuring apparatus according to claim 19, further comprising:
an exposure-time changer configured to change an exposure time for the polarization component by each of the first and second detectors, wherein:
the image formation processor forms the image of the measurement object, based on the first and second detection signals originating from the polarization components detected in the changed exposure time and based on the fourth detection signal.

24. An optical image measuring apparatus according to claim 23, wherein:
the first and second detectors output the first and second detection signals, respectively, at a specific frame rate; and
the exposure-time changer changes the exposure time by each of the first and second detectors to a time shorter than the specific frame rate.

25. An optical image measuring apparatus according to claim 23, wherein:
the first and second detectors output the first and second detection signals, respectively, at a specific frame rate;
the light-emitting part emits the broadband light whose emission time is shorter than the specific frame rate; and
the exposure-time changer changes the exposure time by each of the first and second detectors to a time shorter than the emission time of the broadband light.

26. An optical image measuring apparatus according to claim 19, wherein:
   the image formation processor includes:
   a background-light calculator configured to calculate a background light component of the interference light, based on the fourth detection signal; and
   an interference-component-intensity calculator configured to calculate a signal intensity of an interference component of each of the two polarization components, based on the calculated background light component and the first and second detection signals; and
   the image formation processor forms the image of the measurement object, based on the calculated signal intensity of the interference component of each of the two polarization components.

27. An optical image measuring apparatus according to claim 19, wherein:
   the image formation processor includes:
   a background-light calculator configured to calculate a background light component of the interference light, based on the fourth detection signal; and
   a phase-distribution calculator configured to calculate a spatial phase distribution of the interference light, based on the calculated background light component and the first and second detection signals; and
   the image formation processor forms an image showing the calculated spatial phase distribution.

28. An optical image measuring apparatus according to claim 19, wherein:
   the first and second detectors output the first and second detection signals, respectively, at a specific frame rate;
   the light-emitting part intermittently emits a flash light as the broadband light at a timing synchronized with the specific frame rate, when the optical-path-length changing member is inserted into the optical path; and
   for each of the flash lights emitted intermittently, the image forming processor forms the image of the measurement object, based on the first and second detection signals originating from the flash light and based on the fourth detection signal.

\* \* \* \* \*